United States Patent [19]

Takatsu et al.

[11] Patent Number: 5,760,204

[45] Date of Patent: Jun. 2, 1998

[54] DNA ENCODING MURINE INTERLEUKIN-5 RECEPTOR

[75] Inventors: Kiyoshi Takatsu; Akira Tominaga; Satoshi Takagi, all of Kumamoto, Japan

[73] Assignee: Kiyoshi Takatsu, Japan

[21] Appl. No.: 442,282

[22] Filed: May 16, 1995

Related U.S. Application Data

[62] Division of Ser. No. 757,309, Sep. 10, 1991, Pat. No. 5,453,491.

[30] Foreign Application Priority Data

Sep. 11, 1990 [JP] Japan .................... 2-40638

[51] Int. Cl.$^6$ .................... C12N 15/24; C12P 21/00; C07H 21/07
[52] U.S. Cl. .................... 536/23.5; 435/69.1; 435/252.3; 435/320.1; 435/361; 435/365
[58] Field of Search .................... 536/23.5; 435/69.1, 435/172.3, 252.3, 320.1, 361, 365

[56] References Cited

U.S. PATENT DOCUMENTS

| 4,859,609 | 8/1989 | Dull et al. .................... 436/501 |
| 5,006,459 | 4/1991 | Kung et al. .................... 435/5 |

FOREIGN PATENT DOCUMENTS

| 8928720 | 7/1989 | Australia . |
| A-0 325 474 | 7/1989 | European Pat. Off. . |
| A-0 367 566 | 5/1990 | European Pat. Off. . |
| 0 492 214 A2 | 1/1992 | European Pat. Off. . |
| WO-A-9 007 518 | 7/1990 | WIPO . |

OTHER PUBLICATIONS

Takaki et al., 1991, Identification of the second subunit of the murine interleukin-5 receptor: interleukin-3 receptor-like protein, AIC2B is a component of the high affinity interleukin-5 receptor, *The Embo Journal* 10(10):2833-2838.

Migita et al., *Cell. Immunol* 133, 1991, pp. 484-497.

Hitoshi, et al., 1989, "Interferon-gamma inhibits the proliferation but not the differentiation of murine B cells in response to IL-5", Int. Immunol., 1(2):185-90.

Hitoshi et al., 1990, "Distribution of IL-5 receptor-positive B cells", J. of Immunol., 144:4218-25.

Kinashi et al., 1986, "Cloning of complementary DNA encoding T-cell replacing factor and identify with B-cell growth factor II", Nature, 324(6092):70-73.

Matsumoto et al., 1989, Interleukin-5 induces maturation but not class switching of surface Iga-positive B cells into IgA-secreting cells, Immunology, 66:32-38.

Migita et al., 1991, "Characterization of the human IL-5 receptors on eosinophils", Cell. Immunol., 166:484-97.

Mita et al., 1988, "Receptors for T cell-replacing factor/ interleukin 5", J. Exp. Med., 168:863-78.

Mita et al., 1989, "Rapid methods for purification of human recombinant interleukin-5 (IL-5) using the anti-murine IL-5 antibody-coupled immunoaffinity column", J. Immunol. Methods, 125:233-41.

Mita et al., 1989, "Characterization of high-affinity receptors for interleukin 5 on interleukin 5-independent cell lines", Proc. Natl. Acad. sci. USA 86:2311-15.

Murata et al., 1990, "Interleukin 5 and interleukin 3 induce serine and tyrosine phosphorylations of several cellular proteins in an interleukin 5-dependent cell line", Biochem. and Biophys. Res. Comm., 173(3):1102-08.

Sanderson et al., 1988, "Molecular and cellular biology of eosinophil diferentiation factor (interleukin-5) and its effects on human and mouse B cells", Immunological Reviews, 102:29-50.

Sonoda et al., 1989, "Transforming growth factor $\beta$ induces Iga production and acts additively with interleukin 5 for IgA production", J. Exp. Med., 170:1415-20.

Spry, Christopher J.F., 1988, Eosinophils: a comprehensive review, and guide to the scientific and medical literature, Oxford University Press, 262-287.

Takaki et al., 1990, "Molecular cloning and expression of the murine interleukin-5 receptor", EMBO Journal, 9(13):4367-74.

Takatsu et al., 1988, "T cell-replacing factor (TRF)/interleukin 5 (IL-5); molecular and functional properties", Immunological Reviews, 102:107-135.

Takatsu and Tominaga, 1990, "Interleukin 5 as a hematopoietic cell growth and differentiation factor", Growth Factors, Differentiation Factors, and Cytokines, A. Habenicht (ed.), 147-62.

Tominaga et al., 1988, "Molecular properties and regulation of mRNA expression for murine T cell-replacing factor/ IL-5", J. Immunol., 140(4):1175-81.

Tominaga et al., 1989, "Establishment of IL-5 dependent early B cell lines by long-term bone marrow cultures", Growth Factors, 1:135-46.

Tominaga et al., 1990, "Role of carbohydrate of moiety of IL-5", J. Immunol., 144(4):1345-52.

Yamaguchi et al., 1989, "Mechanisms of the interleukin 5-induced differentiation of B cells", 106(5):837-843.

(List continued on next page.)

*Primary Examiner*—Garnette D. Draper
*Attorney, Agent, or Firm*—Pennie & Edmonds

[57] ABSTRACT

The invention provides an isolated cDNA sequence coding for murine interleukin 5 receptor, murine secretory interleukin 5 receptor, human interleukin 5 receptor, and human secretory interleukin 5 receptor and products including murine interleukin 5 receptor, murine secretory interleukin 5 receptor, and human interleukin 5 receptor which are produced using the isolated cDNA sequence. These products may be useful for a therapeutic agent for autoimmune disorders and diseases with eosinophilia in which human IL-5 is believed to be involved.

10 Claims, 10 Drawing Sheets

OTHER PUBLICATIONS

Yamaguchi et al., 1990, "Characterization of the murine interleukin 4 receptor by using a monoclonal antibody", Int. Immunol., 2(2):181–187.

Mita al., Pnas 86, pp. 2311–2315 (1989).

Devos et al., Embo 10(8) 1991, pp. 2133–2137.

Devos et al., Biochem. Biophys. Res. Comm. 172(2) p. 570–575 (1990).

Kaczmerski et al., Blood Res. 5(3) pp. 193–203 (1991).

Tavernier et al., Pnas 89 pp. 7041–7045 (1992).

Hitoshi et al., J. Immunol., 144 pp. 4218–4225 (1990).

Cosman, DNA and Protein Engineering Techniques vol. 2(1) pp. 1–3 (1990).

Dower et al., J. Clin. Immunol. 10(6) pp. 289–299 (1990).

Bazan, Immunol. Today 11(10) pp. 350–354 (1990).

Takaki et al., Lymphokine Research 9:572, 1990.

Gearing et al., Embo Journal 8:3667–3676, 1989.

Yamaguchi et al., International Immuno. 2:181–188, 1990.

Rolink et al., J.Exp. Med. 169:1693–1701, 1989.

Takaki et al., "Embo Journal "9:4367–4374, 1990.

Tavernier et al., Cell 66 1175–1184, 1991.

DNA ENCODING MURINE INTERLEUKIN-5 RECEPTOR

This is a division of application Ser. No. 07/757,390, filed Sep. 10, 1991 now U.S. Pat. No. 5,453,491.

BACKGROUND OF THE INVENTION

1. Field of the Invention

The present invention relates to isolated cDNA sequences coding for murine interleukin 5 receptors, murine secretory interleukin 5 receptors and human interleukin 5 recepters and to murine interleukin 5 receptors, murine secretory interleukin 5 receptors and human interleukin 5 receptors which are produced using the isolated cDNA sequences as well as to methods of producing the interleukin 5 receptors.

2. Prior Art

Interleukin 5 (referred to as "IL-5", hereinafter) is a proliferation and differentiation factor for eosinophils and B lineage cells (Immunol. Rev. 102: 29, 107.,1988). It has been known that IL-5 is produced especially by T cells primed with *Mycobacterium tuberculosis*, parasites or alloantigens (J. Immunol. 140: 1175, 1988; Nature, 324: 70, 1986). IL-5 has also been known to induce production of IgM class immunoglobulin including anti-DNA antibody. Recently, IL-5 has been suspected of involvement in autoimmune diseases and there is a report that IL-5 is closely associated with eosinophilia accompanied by autoantibody production, fascitis and myositis(Eosinophils, Oxford University Press, 1988).

There are two types of IL-5 receptors (referred to as "IL-5R", hereinafter), namely, membrane bound IL-5R and secretory IL-5R. Among them, mouse secretory IL-5R is able to bind to human IL-5 and therefore expected to serve as a therapeutic agent for diseases associated with IL-5.

The inventors have obtained IL-5 responsive early B cells, T 88 and T-88M by culturing mouse bone marrow cells in the presence of IL-5 (Growth Factors 1: 135 1989) and produced IL-5R. The cross-linking reaction and subsequent SDS-PAGE analysis have revealed that IL-5R comprises at least two types of subunits, one having a molecular weight of about 46,500 and the other having a molecular weight of about 114,000, and that there are two types of IL-5R, a low affinity IL-5R having the dissociation constant of 27 nM and a high affinity IL-5R having the dissociation constant of 150 pM. It has been believed that the low affinity IL-5R comprises the small subunit of an estimated molecular weight of 46,500 while a high affinity IL-5R comprises the large subunit (MW: 114,000) and the small subunit (46,500) (Proc. Natl. Acad. Sci. U.S.A. 86: 2311, 1989).

The inventors have produced H7 and T21 monoclonal antibodies by immunizing rats with a membrane fraction of T88-M cells, which inhibit the binding of IL-5 to IL-5R (Int. Immunol. 2: 181, 1990; J. Immunol. 144: 4218, 1990). Anti-IL-5R antibodies, H7 and T21, are found to bind to glycoprotein of the molecular weight of about 60,000 according to the SDS-PAGE analysis. The real molecular weight of the small subunit is found to be about 55,000 according to the binding assay using IL-5 free of an oligosaccharide, suggesting that the low affinity IL-5R comprises a single molecule of molecular weight of about 60,000 (Int. Immunol. 2: 181, 1990).

We have also reported recently that IL-5R is found on the cell surface of human eosinophils. The dissociation constant of human IL-5R is 170–330 pM and the molecular weight is 55,000–60,000 according to the SDS-PAGE analysis.

Human IL-5R appears to be comparable to a low affinity murine IL-5R (Migita, M., Yamaguchi, N., Mita, S:, Higuchi, S., Hitoshi, Y., Yoshida, Y., Tomonaga, M., Matsuda, I., Tominaga, A., Takatsu, K., 1991, Cellular Immunology, 133: 484–497).

There has been no report on the isolation of a DNA sequence coding for the low affinity murine/human IL-5R. An object of the invention is to isolate the DNA sequence coding for the low affinity murine/human IL-5R and to determine the DNA sequence. The isolated DNA sequence may be used to produce murine/human IL-5R in mammalian cells. Another object of the invention is to obtain a DNA sequence coding for secretory IL-5R which is distinct from the DNA sequence coding for membrane bound IL-5R and to produce pure secretory IL-5R using the DNA.

The present invention is characterized by the following description:

(1). An isolated cDNA sequence coding for murine interleukin 5 receptor which is synthesized from murine-early B cell mRNA.

(2). The isolated cDNA sequence of (1) wherein the nucleotide sequence comprises the open reading frame sequence described in SEQ ID No.1.

(3) The isolated cDNA sequence of (1) wherein the nucleotide sequence comprises the entire sequence described in SEQ ID No.2.

(4). An isolated cDNA sequence coding for secretory murine IL-5R which is synthesized from murine early B cell mRNA.

(5) The isolated cDNA sequence of (4) wherein the nucleotide sequence comprises the open reading frame sequence described in SEQ ID No.3.

(6). The isolated cDNA sequence of (4) wherein the nucleotide sequence comprises the entire sequence described in SEQ ID No.4.

(7). An isolated murine interleukin 5 receptor wherein the amino acid sequence comprises the sequence described in SEQ ID No.5.

(8). An isolated murine interleukin 5 receptor wherein the amino acid sequence comprises the sequence-described in SEQ ID No.6.

(9) An isolated murine secretory interleukin 5 receptor wherein the amino acid sequence comprises the sequence described in SEQ ID No.7.

(10) An isolated murine secretory interleukin 5 receptor wherein the amino acid sequence comprises the sequence described in SEQ ID No.8.

(11). A method of producing the murine interleukin 5 receptors which comprises culturing cells capable of expressing the murine interleukin 5 receptors in medium and isolating the murine interleukin 5 receptors from the cells or the culture supernatant using anti-interleukin 5 receptor antibodies.

(12) A COS 7 monkey cell (ATCC CRL1651) transfected with a recombinant vector containing the cDNA sequence of any one of (1)–(6).

(13) A method of producing the murine interleukin 5 receptors and the murine secretory interleukin 5 receptors comprises culturing the COS 7 cell transfected with relevant DNA in medium, and recovering the murine interleukin 5 receptors from the cells or secretory murine interleukin 5 receptors from the culture supernatant.

(14). An isolated cDNA sequence coding for human interleukin 5 receptor which is synthesized from mRNA of a human peripheral blood eosinophil.

(15). The isolated cDNA sequence of (14) wherein the nucleotide sequence described in SEQ ID No. 9 comprises the open reading frame sequence coding for human interleukin 5 receptor.

(16). The isolated cDNA sequence of (14) wherein the nucleotide sequence described in SEQ ID No.10 comprises the entire sequence coding for human interleukin 5 receptor.

(17). The isolated cDNA sequence of (14) wherein the nucleotide sequence described in SEQ ID No. 11 comprises the open reading frame sequence coding for human interleukin 5 receptor 2.

(18). The isolated cDNA sequence of (14) wherein the nucleotide sequence described in SEQ ID No. 12. comprises the entire sequence coding for human interleukin 5 receptor 2.

(19). An isolated human interleukin 5 receptor wherein the amino acid sequence comprises the sequence described in SEQ ID NO.13.

(20). An isolated human interleukin 5 receptor wherein the amino acid sequence comprises the sequence described in SEQ ID NO.14.

(21). The isolated cDNA sequence of (14) coding for a whole or part of amino acid residue numbers 1–333 described in SEQ ID No. 13

(22). A secretory human interleukin 5 receptor which lacks a cytoplasmic region and a transmembrane region of human interleukin 5 receptor.

(23). An expression vector comprising the cDNA sequence of any one of (14), (15), (16), (17), (18), and (21).

(24). A method of producing the secretory human interleukin 5 receptor and its analogues which comprises culturing a recombinant vector coding for the secretory human interleukin 5 receptor under the conditions which promote the expression thereof and recovering the secretory human interleukin 5 receptor.

SUMMARY OF THE INVENTION

The invention provides isolated DNA sequences coding for murine/human IL-5R and pure murine IL-5R produced by a genetic engineering technique using the isolated DNA sequence as well as an isolated DNA sequence coding for secretory murine IL-5R. The DNA sequence coding for secretory murine IL-5R is especially valuable in constructing a nucleotide sequence corresponding to the sequence of secretory human IL-5R and in producing secretory human IL-5R using the DNA sequence. The secretory human IL-5R thus produced may be utilized as a therapeutic agent for autoimmune disorders or diseases with eosinophilia in which IL-5 is believed to be involved and may greatly contribute to the medical and pharmaceutical field.

BRIEF DESCRIPTION OF THE DRAWINGS

The Invention is explained referring to the attached drawings.

DETAILED DESCRIPTION OF THE INVENTION

The description which relates to murine IL-5R is indicated (Murine) and which relates to human IL-5R is indicated (Human).

Preparation of Poly(A)$^+$ RNA from Mouse Bone Marrow Cells (Murine)

In order to prepare the cDNA coding for the IL-5R, mRNAs are recovered from the mouse bone marrow cells having IL-5R. Mouse bone marrow cells are obtainable by a long-term bone marrow cell culture in the presence of IL-5 (Growth Factor 1: 135, 1989). A suitable source of cells may be a Balb/c mouse bone marrow long-term culture cell line, Y16, which is early B cells and shows a strong response to IL-5 (even at a concentration of 1 pg/ml of IL-5). RNA is prepared from the cell according to the method described by Okayama et al. (Methods in Enzymology 154: 3 1987). Poly(A)$^+$ RNA is recovered by fractionating the total RNA with the affinity chromatography using an oligo (dT) cellulose column.

Construction of cDNA Library from mRNA (Murine)

The poly(A)+ RNA is reverse transcribed to cDNA using random primers and reverse transcriptase (Gene 25: 263, 1983). The cDNA larger than 1.0 kb is selected for cloning and inserted into the BstXI site of CDM 8 vector (see FIG. 2A) containing a cytomegalovirus promoter according to the method described by Seed et al. (Proc. Natl. Acad. Sci. U.S.A. 84: 8573, 1987). E. coli is transformed with the recombinant plasmid in order to provide cDNA library expressible in mammals.

Cloning of IL-5R Gene: Transfection of COS7 Cells Using the DNA of the Transformant (Murine)

COS 7 cells (Green monkey kidney cells) are transfected with the DNA according to the DEAE dextran or protoplast fusion method. The COS7 transformant is screened using anti-IL-5R antibodies H7 and T21 according to the method described by Seed et al. (Nature 329: 840, 1988). H7 and T21 antibodies and the COS7 suspension are incubated together. After incubation, the mixture is transferred to plates coated with goat anti-rat IgG antibody (H7 and T21 are rat IgG antibodies). Then, plasmid DNA is recovered from the COS7 cells immobilized on the bottom of the plate. The transformation-screening procedure described above is repeated several times. After screening, a group of the selected COS7 transformant is further screened by flow cytometry using fluorescein-conjugated H7 and T21 and the transformant containing IL-5R cDNA is identified.

The Entire Structure of murine IL-5R Genes (Murine)

Figure 1:
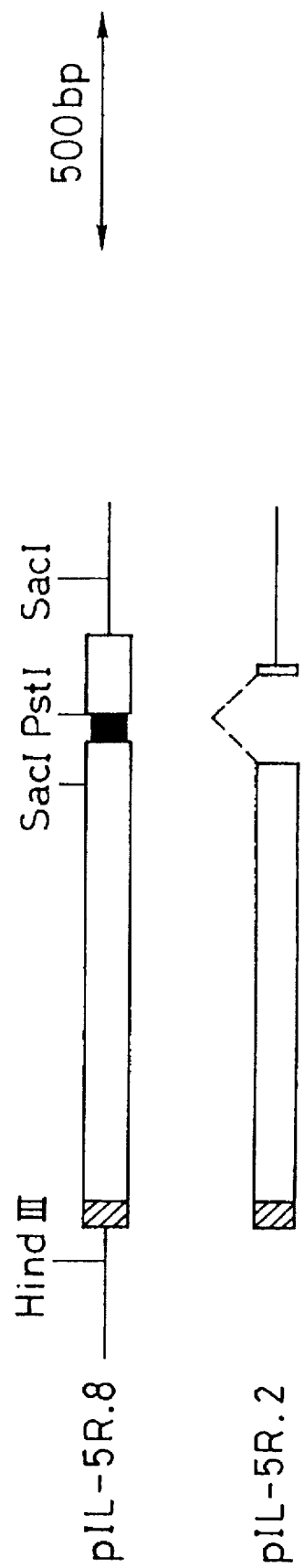
FIG. 1 shows partial restriction maps of two IL-5R cDNA clones. The box indicates an open reading frame which is expected to be translated. The shaded portion at the 5'-end indicates a signal peptide, and the solid portion indicates the transmembrane region.

The rough restriction maps of IL-5R cDNA isolated above are shown in FIG. 1. pIL-5R.8 is the cDNA clone prepared first from the CDM 8 library. pIL-5R.2 is obtained from the cDNA library using the HindIII-PstI fragment of pIL-5R.8 as a probe according to the colony hybridization method.

The nucleotide sequences of the cDNA fragments of pIL-5R.2 and pIL-5R.8 are determined according to the method described by Sanger et al (Proc. Natl. Acad. Sci. U.S.A., 74: 5463, 1977). The entire nucleotide sequence of the cDNA fragment of pIL-5R.8 and the deduced amino acid sequence are shown in SEQ ID No.15. The nucleotide A of the initiation codon ATG is numbered 303 and the amino acid methionine is numbered 1. The cDNA fragment of pIL-5R.8 has 1808 nucleotides in length which codes for 415 amino acids. This polypeptide consists of 4 portions according to Hydropathy plot (OF URFS and ORFS, Rusell F. Doolittle, University Science Books, 1987): signal peptide (See amino acids 1-17 of SEQ ID NO.15), extracellular region, transmembrane region, and cytoplasmic region. The amino acids at positions 32-34, 128-130, 213-215, 241-243, 392-394, and 412-414 of SEQ ID No.15 are presumably linked to N-linked oligosaccharide. pIL-5R.2 lacks a transmembrane region (FIG. 1 and SEQ ID No. 16) and therefore, IL-5R expressed by pIL-5R.2 is a secretory type. As shown in SEQ ID No.16, pIL-5R.2 lacks the sequence between the nucleotide Nos. 986 and 1164

Expression of IL-5R gene (Murine)

Figure 2:
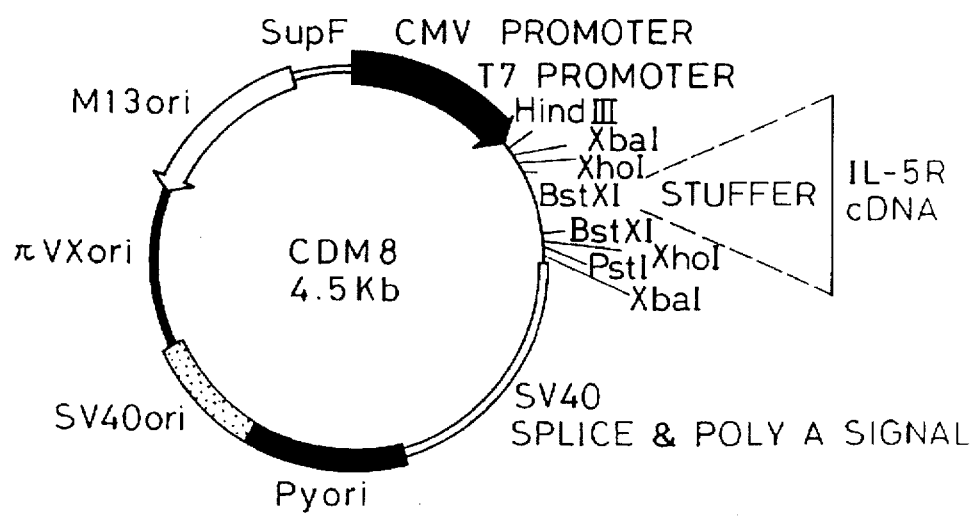
FIG. 2A–2B shows vectors used in the present invention and a site of inserting an isolated DNA into the vector.
Figure 2:
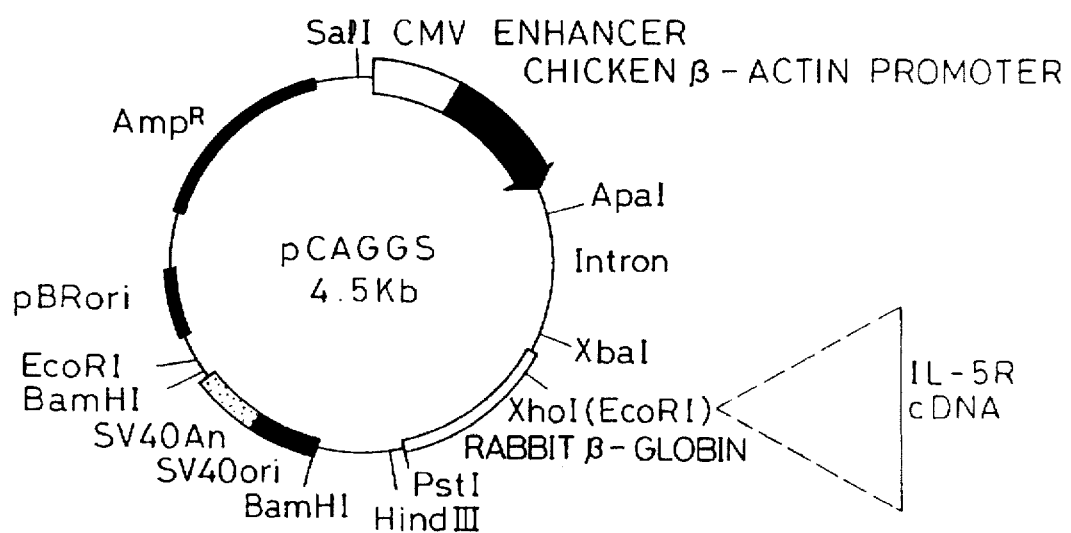

The following two types of vectors, CDM8 and pCAGGS, can be utilized as expression vectors for an isolated IL-5R cDNA sequence (see FIG. 2).

CDM 8 vector: The vector demonstrates an elevated DNA expression in mammalian cells. The vector has two BstXI sites. The vector is digested with BstXI and both ends of cDNA of interest are ligated to a BstXI linker. The cDNA-linker complex is ligated to the BstXI digested vector.

pCAGGS vector: The vector contains a CMV enhancer upstream of the promoter of pAGS-3, which is a vector having a much stronger expression ability than that of CDM8 (Gene, 79:269, 1989). The cDNA insertion site of pCAGGS is XhoI site substituted with EcoRI site in the exon of rabit β-globin gene region. The pCAGGS vector demonstrate a higher level of DNA product expression than pAGS-3.

In the Example of the invention, the pCAGGS vector is used for expression test of IL-5R and the expressed murine IL-5R is tested by IL-5 binding test, IL-5 cross-linking test and immunoprecipitation test using monoclonal antibody, H7.

The murine IL-5R cDNA encoding a secretory IL-5R is inserted into the XhoI (EcoRI) site of the pCAGGS vector. COS7 (Green monkey kidney cell, ATCC CRL1651) is transfected with the recombinant plasmid and the resulting transformant is grown in a medium. The amino acid sequence of the peptide in the culture supernatant is determined. The N-terminal 20 amino acids thus determined are the same as those deduced from the nucleotide sequence of the murine IL-5R cDNA. The COS7 culture supernatant containing soluble IL-5R inhibits the binding of IL-5 to IL-5R expressed on B cells or eosinophils.

Binding Assay of IL-5R to IL-5 (Murine)

The COS7 transformant thus obtained is tested for the production of IL-5R capable of binding to IL-5 using $^{35}$S-methionine and $^{35}$S-cysteine labeled IL-5 (J. Immunol. 140: 1175, 1988; J. Exp. Med. 168: 863, 1988). Binding of the labeled IL-5 is inhibited by the excess amount (100-fold) of the non-labelled IL-5 and thus the cDNA clone pIL-5R.8 is confirmed to code for IL-5R.

Cross-linking of IL-5R to IL-5 and Immunoprecipitation of IL-5R to IL-5 (Murine)

COS7 cells are transfected with pIL-5R.8 followed by cross-linking reaction and immunoprecipitation.

Cross-linking: IL-5R produced by the transformant is tested whether it is the same as those expressed by a IL-5 responsive early B cell, T88-M, by the cross-linking test using $^{35}$S-labeled IL-5 (Proc. Natl. Acad. Sci. U.S.A., 1989, 86: 2311). After electrophoresis, the band pattern on the gel indicates that the molecular weight comparable to IL-5 monomer is decreased (about 22,000) under reduced condition.

Immunoprecipitation: The surface proteins of the transfected cells is $^{125}$I-labeled and immunoprecipitated with anti-IL-5R antibodies, H7 (Int. Immunol. 2: 181, 1990). IL-5R produced by the transformant are found to have a molecular weight of 60,000.

Cell Lines Expressing IL-5R mRNA and the Size of the IL-5R mRNA (Murine)

Poly(A)+ RNA are prepared from IL-5 responsive cell lines such as Y16 (early-B cell), BCL1-B20 (mouse B cell chronic leukemia lymphoma, in vitro line); mouse myeloma cell, MOPC104E, X5568, L cell, IL-3 responsive cell line FDC-P1 derived from mouse bone marrow long-term cultured cell, and IL-2 responsive mouse T cell lines. 2 μg of each of poly(A)+ RNA are tested for the presence of IL-5R MRNA by Northern blot.

Northern blot is carried out using the HindIII-PstI fragment of pIL-5R.8 as a probe (Biochemistry 16:4743, 1977). IL-5 responsive cell lines including Y16, BCL1-B20, MOPC104E are found to express IL-5R mRNA with the size of 5–5.8 kb

Preparation of Poly(A)+ RNA from Human Peripheral Blood Eosinophils (Human)

A DNA sequence coding for human IL-5R is prepared from human peripheral blood eosinophils. Eosinophils are isolated from peripheral blood of healthy volunteers and of a patient with eosinophilia by a density gradient centrifugation using Ficoll (Migita, Y., et al. supra). Whole mRNA is prepared from eosinophils according to the method described by Okayama et al. (ibid). Poly(A)⁺ RNA is recovered by fractionating the whole RNA with the affinity chromatography using an oligo (dT) cellulose column. One of the poly(A)⁺ RNA preparation is derived from healthy volunteers and the other is derived from a patient with eosinophilia.

Construction of cDNA Library from mRNA (Human)

The poly(A)⁺ RNA is reverse transcribed to cDNA using random primers and reverse transcriptase as described above. The cDNA of more than 1.0 kb fragments is selected for cloning. The cDNA fragment derived from eosinophils of healthy volunteers (helv-cDNA) is inserted into the BstXI site of vector pAGS-3 (Miyazaki, et al., 1989, Gene, 79: 269) according to the method described by Seed et al. (ibid). E. coli is then transformed with the recombinant plasmid (helv-cDNA library). The cDNA derived from eosinophils of patients with eosinophilia (eosi-cDNA) is inserted into the EcoRi site of phage λgt10 using an EcoRI linker. E. coli is then infected with the recombinant phage (eosi-cDNA library).

Screening of helv-cDNA and eosi-cDNA Libraries for Human IL-5R (Human)

The helv-cDNA library is screened using the HindIII-PstI fragment of pIL-5R.8. A positive clone is isolated and is designated as ph5R.1. ph5R.1 lacks some of the nucleotide sequence of IL-5R. Subsequently, the eosi-cDNA library is screened using the nucleotide sequence of ph5R. 1. Two positive clones designated as HSIL5R and HSIL5R2 are isolated.

Human IL-5R Gene Structure (Human)

Figure 6:
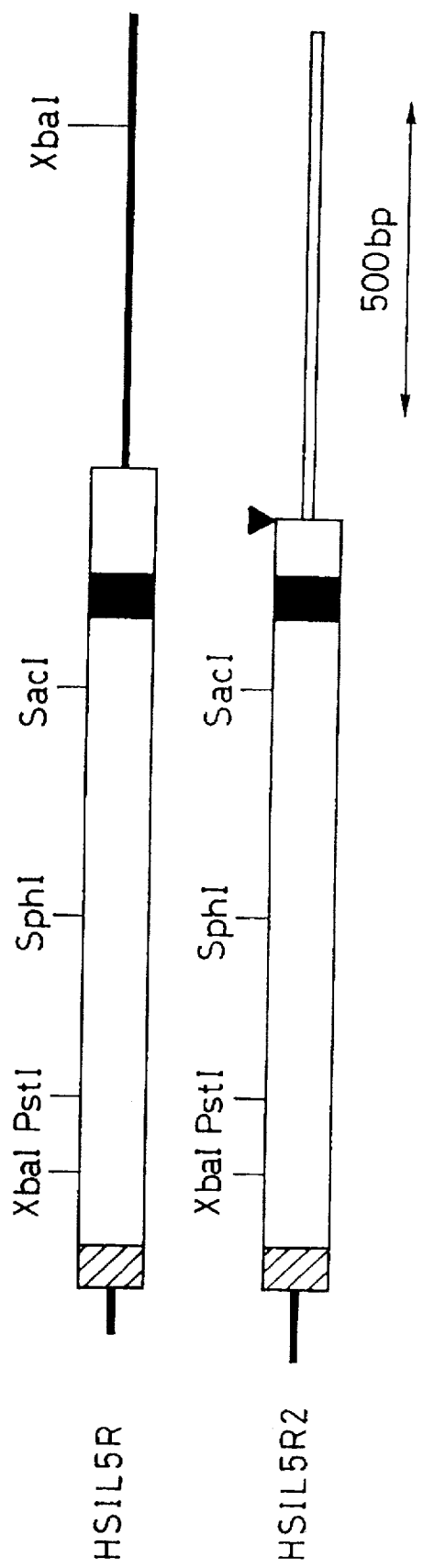
FIG. 6 shows a restriction map of a human IL-5R cDNA fragment of HSIL5R and HSIL5R2. The box represents the open reading frame of IL-5R. The 5' end hatched box is a putative signal peptide and the solid box is the predicted transmembrane region. The mark ▼ indicates the starting point of the nucleotide sequence which distinguishes HSIL5R from HSIL5R2.

FIG. 6 shows restriction maps of the isolated IL-5R cDNAs of HSIL5R and HSIL5R2. The nucleotide sequence was determined according to the Sanger's method (ibid). HSIL5R and HSIL5R2 are membrane bound receptors. The cytoplasmic domain sequence of HSIL5R2 is shorter than that of HSIL5R.

SEQ ID No. 17 and No. 18 show the nucleotiode and deduced amino acid sequence of HSIL5R (420 amino acids in length) and HSIL5R2 (396 amino acid in length), respectively. The amino acid sequence is analyzed as described above.

HSIL5R and HSIL5R2 consist of signal peptide region, extracellular region, transmembrane region, cytoplasmic region. The nucleotide sequence downstream of nucleotide position 1245 distinguishes HSIL5R (SEQ ID No.17) from HSIL5R2 (SEQ ID No.18). The amino acid sequence of HSIL5R2 terminates after amino acid Ile (amino acid number 396) located immediately after the nucleotide position 1245.

Expression of Human IL-5R (Human)

Human IL-5R cDNA is inserted into a pCAGGS vector, and COS 7 cells are transfected with the recombinant plasmid. λgt10 cDNA clones, HSIL5R and HSIL5R2 are digested with EcoRI and the IL-5R cDNA fragment is inserted into the EcoRI site of pCAGGS.

Binding Assay of transfectants with HSIL5R or HSIL5R2 to IL-5 (Human)

The IL-5R expression of the clones are tested using $^{35}$S-methionine- and $^{35}$S-cysteine-labeled murine IL-5 or $^{125}$I-labeled human IL-5. The human IL-5 is prepared as follows:

The IL-5 cDNA fragment is inserted into an expression vector derived from baculovirus. Sf21 cells (Spodotera frugiperda) are infected with the recombinant DNA. The cells are cultured and the culture supernatant is tested for human IL-5 using anti-IL-5 monoclonal antibody, NC17 (Proc. Natl. Acad. Sci. U.S.A. 84: 4581, 1987). The isolated human IL-5 is labeled with $^{125}$I. Binding assay is carried out as described for murine IL-5R.

Cross-linking of IL-5R to IL-5 (Human)

IL-5R produced by the positive clones is tested whether it is the same as those produced by eosinophils, by cross-linking test using $^{35}$S-labeled murine IL-5 and $^{125}$I-labeled human IL-5 as described above.

Cell Lines Expressing IL-5R mRNA and the Size of the IL-5R mRNA (Human)

Poly(A)⁺ RNA may be prepared from human eosinophils, erythroleukemic cell line TF-1, eosinophilic leukemia cell line EoL-3, ATL-2 adult T cell leukemia cell line ATL-2, Burkitt's lymphoma cell line Raji, and histiocytic lymphoma cell line U-937. 6 µg of each of poly(A)⁺ RNA is tested for the presence of IL-5R mRNA using the entire sequence of HSIL5R cDNA as a probe. Human eosinophils and TF-1 cell line are found to express IL-5R mRNA with the size of 1.4 kb and 5.3 kb.

Production of Secretory Human IL-5R

HSIL5R cDNA is inserted into the EcoRI site of Bluescript SK (−). The construct is digested with SalI and KpnI. The SalI-KpnI digested fragment is then incubated with exonuclease III so that the sequence coding for the cytoplasmic domain and transmembrane domain of human IL-5R can be removed. The digested fragment is blunted with mung bean exonuclease followed by a treatment with a klenow fragment and subjected to ligation (Gene 33: 103, 1985). After treatment, a clone is obtained which contains deletion from 3' end to the nucleotide number 995 (SEQ ID No. 17), a site which corresponds to the starting point of deletion in the secretory murine IL-5R cDNA. The deletion mutant is digested with EcoRI and BssHII. The resulting DNA fragment is ligated to a linker containing a stop codon. After ligation, a DNA-linker complex is inserted into an appropriate restriction site of any vector. Alternatively, the HSIL-5R cDNA fragment of the Bluescript SK(−) construct is deleted from 3' end to the nucleotide number 996. As a result of frameshift, the construct contains two stop codons. The secretory human IL-5R construct thus obtained lacks DNA sequences for a cytoplasmic domain and a transmembrane domain and codes for 333 amino acids.

The secretory human IL-5R construct is introduced into host cells and the transfectant produces a secretory human IL-5R. An expression vector is selected according to host cells to be transfected. Host cells include prokaryotes such as gram negative bacteria (E. coli) or gram positive bacteria (Bacillus), yeast, and eukaryotic cell lines derived from insects and mammals.

EXAMPLES

The following Examples are described for murine secretory IL-5R and membrane type IL-5R.

Preparation of Polyadenylated RNA from Y16 Cell (Murine)

Y16 (2×10⁷) cells were placed in a 3 liter Spinner culture bottle containing a medium (RPMI 1640, 4% FCS, 5×10⁻⁵M 2-mercaptoethanol, 100 U/ml of penicillin, 100 µg/ml of streptomycin) and 300 pg/ml of IL-5. The bottle was sealed and incubated for a week. After incubation, about 5×10⁹ cells were harvested. 1×10⁹ cells were solubilized in 50 ml of 5.5M guanidium thiocyanate solution (pH7.0) containing 25 mM sodium citrate, 0.5% sodium laurylsulcosine, and 0.2M 2-mercaptoethanol according to the method described by Okayama et al. (supra). The cell lysate was layered onto cesium trifluoroacetic acid solution (density: 1.5 g/ml) containing 0.1M EDTA/pH7.0. The mixture was centrifuged at 15° C., at 125,000 g, for 24 hours. After centrifugation, the RNA pellet was dissolved in distilled water containing 10 mM Tris-HCl/pH7.5 and 1 mM EDTA. The RNA solution was loaded onto an oligo (dT) cellulose column and the pass-through was loaded onto the column again (Molecular Cloning, 1989, Chapter 7, p26, Cold Spring Harbor Laboratory Press). The oligo (dT) bounded fraction was eluted and 30 µg of poly(A)+ RNA was recovered.

Construction of cDNA Library in CDM8 (Murine)

30 µg of the poly(A)+ RNA thus obtained was used to synthesize cDNA using a cDNA synthesis kit (BRL, Bethesda, Md.) according to the method described by Seed (supra). The CDM8 vector (see FIG. 2A) was digested with BstXI. After digestion, an approximately 4100 bp fragment was purified by a potassium acetate density gradient centrifugation. The cDNA was ligated to a BstXI linker and a cDNA-linker complex containing cDNA having a size of 1,000 bp or more was selected by a potassium acetate density gradient centrifugation. The fractionated fragments were subjected to ligation with the purified CDM8 vector. *E. coli* MC1061/P3 was transformed with the construct and about 2 million transformants were obtained as a cDNA library.

Screening of the cDNA Library (Murine)

COS7 ($5 \times 10^5$) cells were placed in each of 100 plates (6 cm). The following day, the COS7 cell was transfected with 2 µg of the plasmid DNA (per plate) prepared from the cDNA library according to the DEAE-dextran method. On day 3, the COS7 cells were removed from the plates and incubated with antibodies, H7 and T21. The COS7 cell was screened for the presence of the H7 and T21 antigens using goat anti-rat IgG antibodies (Panning technique). After screening, plasmid DNAs were prepared from the H7 and T21 antigen positive COS7 cells. Then, *E. coli* MC1061/P3 was transformed with the plasmid DNAs. Fresh COS7 cells were fused with the transformants according to the protoplast fusion method. The COS7 cells were screened for the presence of the H7 and T21 antigens according to the Panning technique. After four cycles of the procedure described above, fresh COS7 cells were transformed and the transformant was screened by the Panning technique using goat anti-rat IgG antibody F(ab')$_2$ fragment. This transformation-screening procedure was repeated two times in order to eliminate the contamination of Fc recepter genes. After screening, 50 independent colonies were selected and the plasmid DNA was prepared. Fresh COS7 cells were then transfected with the plasmid DNA and the transformants were tested for the presence of the H7 and T21 antigens. One of the transformants was found to be antigen positive and designated as pIL-5R.8.

The cDNA library prepared from Y16 as described above was screened for the presence of IL-5R cDNA using the fragment inserted in pIL-5R.8 as a probe according to the colony hybridization method (Molecular Cloning, 1989, chapter 1, p90, Cold Spring Harbor Laboratory Press): The HindIII-PstI fragment was prepared from pIL-5R.8 and radiolabeled with $\alpha$-$^{32}$P-dCTP according to the random primer method. The transformants of the cDNA library were grown on a solid LB agarose medium (approximately 10,000 colonies per 10 cm plate) overnight. The colonies were transferred to a nitrocellulose membrane and the DNAs on the membrane were hybridized to the radiolabeled profe. Positive colonies were identified through autoradiography. One of the transformants was isolated and designated as pIL-5R.2.

Nucleotide Sequencing of IL-5R (Murine)

The cDNA fragment of pIL-5R.8 was digested with XbaI and inserted into a M13mp19 vector. The construct was digested with BamHI and KpnI. The BamHI-KpnI digested fragment was then digested with exonuclease III: the fragment was digested up to ten minutes with stopping digestion every minute. The digested fragment was blunted with mungbean exonuclease followed by a treatment with a klenow fragment and subjected to ligation (Gene 33:103, 1985). *E. coli* JM109 was transformed with the constructs to produce different sizes of the M13 deletion mutants. Single-stranded DNAs were prepared from the mutants (Methods in Enzymology 101:58, 1983) and the nucleotide sequence was determined using the M 13 primer, 5'-GTTTTCCCAGTCACGAC-3' according to the Sanger's method. Single-stranded DNA was also prepared from the M13 mutant containing the cDNA fragment of a reversed orientation and the nucleotide sequence was determined as described above. The nucleotide sequence thus obtained from the M13 mutant containing the cDNA fragment of a right orientation was found to be complementary to the one of M13 mutant containing the cDNA fragment of a reversed orientation.

SEQ ID No.15 shows the complete nucleotide sequence of pIL-5R.8. The first 17 amino acids are believed to be the signal peptide (Nucleic. Acids. Res. 14:4683, 1986) and the amino acids from amino acid position 340 to amino acid position 361 are considered to be the transmembrane region according to the hydropathy plot. Amino acids 32–34, 128–130, 213–215, 241–243, 392–394, and 412–414 appear to be sites of N-linked oligosaccharide addition. The previously estimated molecular weight (45,284) of IL-5R differs from the real molecular weight (about 60,000) of IL-5R produced by the COS7 cells transfected with pIL-5.8. The difference of the weight may be due to the addition of N-linked oligosacharide. Nucleotide position 1467 represents the beginning of sequence of pIL-5R.2 The nucleotide sequence of pIL-5R.2 shown in SEQ ID No.16 was determined using primers(17-mers) synthesized based on the nucleotide sequence of pIL.-5R.8, a T7 primer (5'-ATGGAAATTAATACG-3'), and a primer for the 3' end of CDM8 (5'-TGCAGGCGCAGAACTGG-3') according to the Sanger's method. The pIL-5R.2 is a frame shift mutant, resulting in translation termination to give 4 peptides. The polypeptide encoded by pIL-5R.2 is a secretory IL-5R which is likely to act on B cells or eosinophils in the process of differentiation.

Expression and Binding Test of IL-5R cDNA (Murine)

pIL-5R.8 (CDM8 vector) was digested with XhoI and the IL-5R cDNA fragment was inserted into the XhoI site of pCAGGS vector (see FIG. 2B) whose EcoRI site had been replaced with a XhoI site.

The new construct was designated as pCAGGS.5R. 8. *E. coli* was transformed with the construct and the transformant was designated as *E. coli* 5R.8. *E. coli* 5R.8 was deposited with Fermentation Research Institute, Agency of Industrial Science and Technology, ministry of International Trade and Industry of 1-3, Higashi 1-chome, Tsukuba-shi, Ibaraki-ken, 305 Japan and was assigned the accession number FERM BP 3085.

COS7 cells were transfected with pIL-5R.8 or pCAGGS.5R.8 and the cells were harvested two days later. $2-10 \times 10^4$ cells were incubated with different concentrations of $^{35}$S-labeled IL-5 ($2.5 \times 10^8$ cpm/µg) in the presence or absence of 100-fold excess of non-labeled IL-5 at 37° C. for 10 minutes. After incubation, the number of IL-5 binding per cell was counted and the dissociation constant was calculated.

Figure 3A:
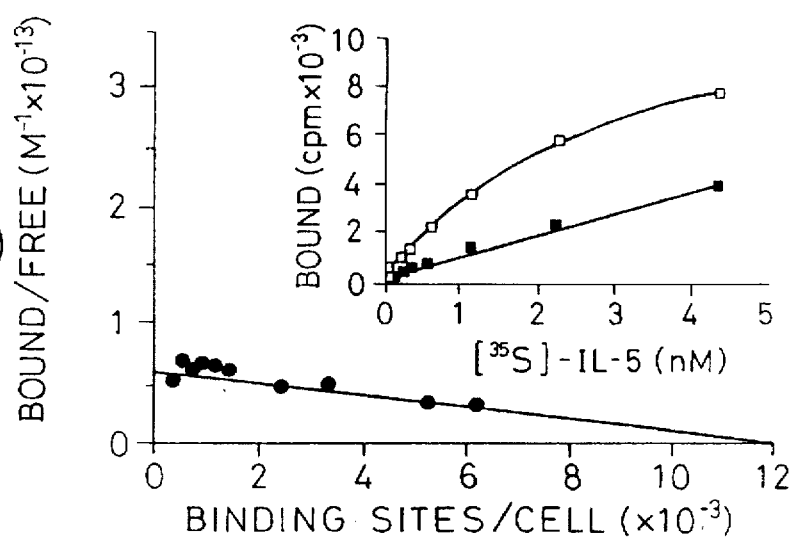
FIG. 3A–3C shows the results of binding assay using $^{35}$S-labeled IL-5 and the Scatchard plot analysis.
Figure 3B:
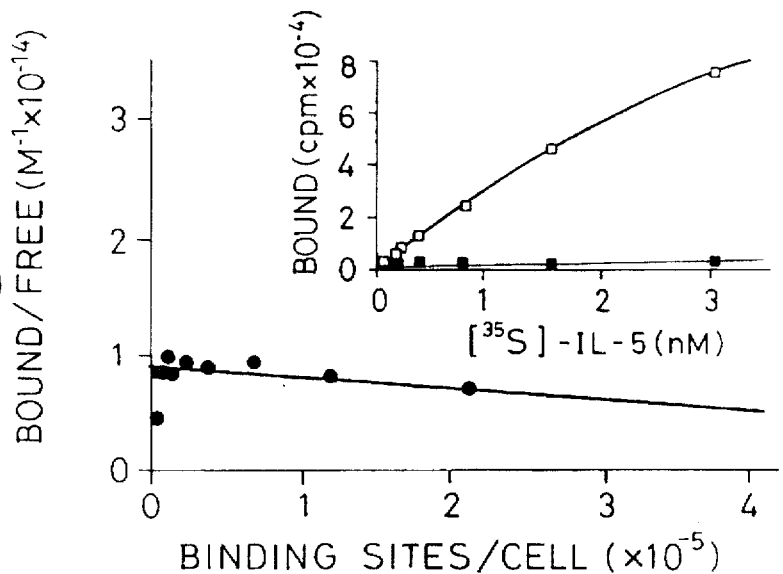
Figure 3C:
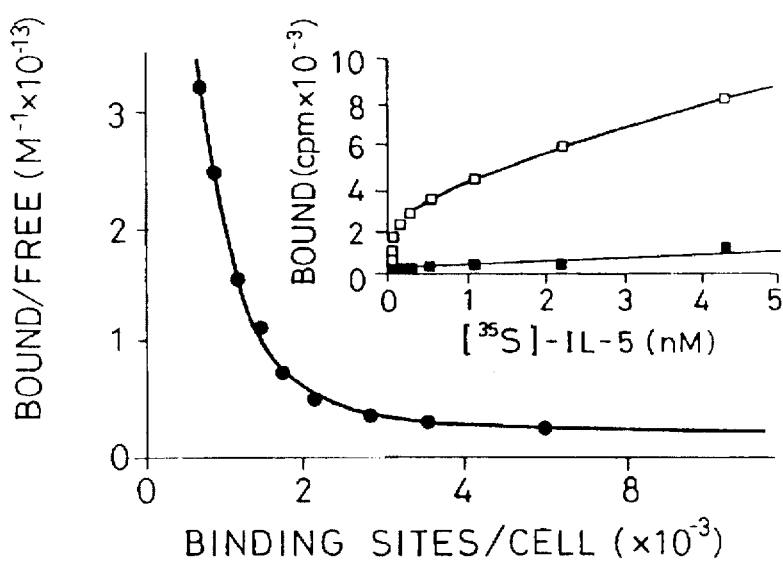

FIG. 3(A), (B), (C) shows the Scatchard plot analysis (Ann N.Y. Acad. Sci, 51: 660, 1949) of $^{35}$S-labeled IL-5 binding to IL-5R expressed on transfectants and Y16 cells. The inset shows the direct binding data (□: total binding, ■: non-specific binding). FIG. 3(A) shows the results when COS7 cells were transfected with pIL-5R.8: the dissociation constant was 2 nM and the number of the IL-5 binding was 12,000/cell. FIG. 3(B) shows the results when COS7 cells were transfected with pCAGGS.5R.8: the dissociation constant was 9.6 nM and the number of the IL-5 binding was 880,000/cell. FIG. 3(C) shows the results when Y16 cells were also tested for the IL-5 binding. A high affinity IL-5R and a low affinity IL-5R were found in the Y16 cells. The high affinity IL-5R has the number of IL-5 binding of 1,200/cell with the dissociation constant ($K_D$) of 20 pM. The low affinity IL-5R has the number of IL-5 binding of 22,000/cell with the dissociation constant ($K_D$) of 5.1 nM. These results suggest that the inserted IL-5R cDNA encodes a low affinity IL-5 recepter.

Cross-linking Test of Low Affinity IL-5R to IL-5 (Murine)

Because COS7 cells transfected with pCAGGS.5R.8 were found to express IL-5R at a higher level than those transfected with pIL-5R.8, pCAGGS.5R.8 was used for the following experiments.

COS7 cells ($1 \times 10^5$) were transfected with pCAGGS or pCAGGS5R.8 and the transformants were incubated with 4 nM $^{35}$S-labeled IL-5 in the presence or absence of 100-fold excess of non-labeled IL-5 as follows: a pCAGGS transformant without non-labeled IL-5 (lane 1), a pCAGGS transformant with non-labeled IL-5 (lane 2), a pCAGGS5R.8 transformant without non-labeled IL-5 (lane 3, 5), a pCAGGS5R.8 transformant with non-labeled IL-5 (lane 4, 6). The mixture was incubated at 37° C. for 10 minutes. Cells were washed extensively and then disuccinimidyl tartarate (DST)(Piece Chemical, Rockford, Ill.) was added to the cell suspension. The cell suspension was incubated at 4° C. for 30 minutes and then 1% Triton X-100 was added to the suspension to disrupt the cells. The disrupted cell suspension was loaded on a 7.5% SDS-polyacrylamide gel in the reducing (lane 5, 6) or non-reducing (lane 1–4) conditions.

Figure 4:
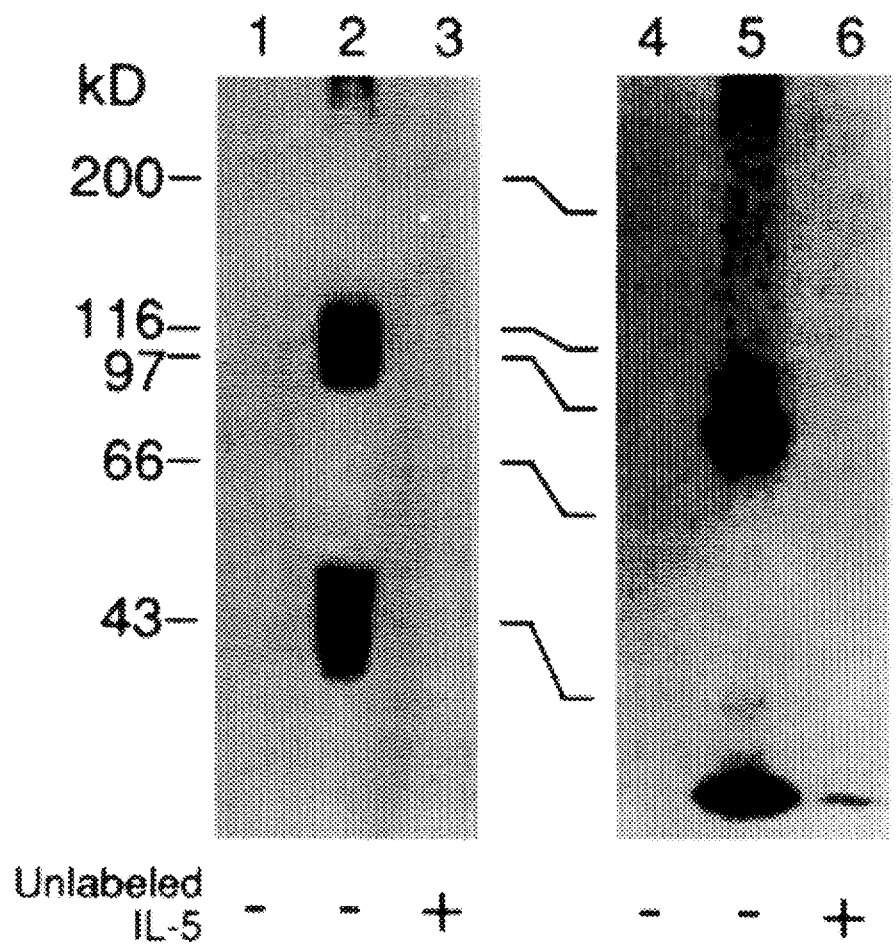
FIG. 4 shows the results of cross-linking experiment using $^{35}$S-labeled IL-5.

After electrophoresis, the gel was analyzed with Bio-Analyzer 100 (Fuji Film). The results are shown in FIG. 4. A band of approximately 90–100 KD in size was found which could be a low affinity IL-5R previously reported by Mita, et al., in Proc. Natl. Acad. Sci. U.S.A. 86: 2311, 1989. In contrast, the molecular weight of the band in the reducing condition was about 75 KD (lane 5 in FIG. 4). The difference was due to the dissociation of monomeric $^{35}$S-labeled IL-5 (MW:22,000) from the IL-5-IL-5R complex, because biologically active IL-5 binds to its receptor as a disulfide-linked dimer.

Immunoprecipitation of IL-5R expressed on pCAGGS.5R.8 Transfected COS7 (Murine)

Figure 5:
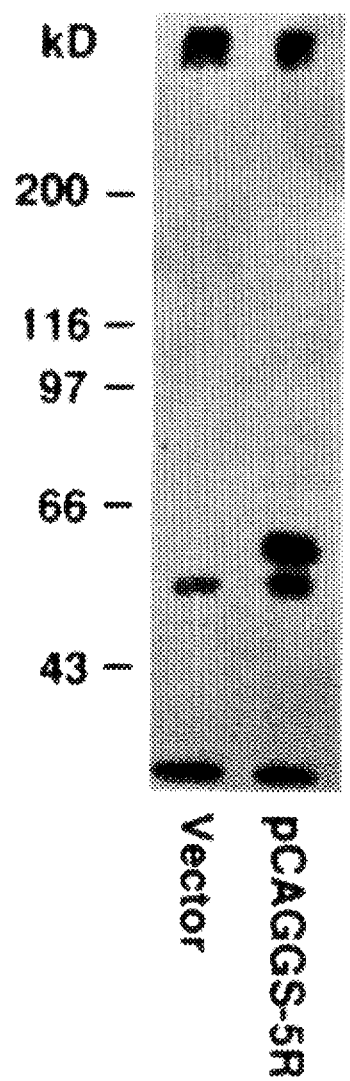
FIG. 5 shows the results of immunoprecipitation of the translated product of mouse IL-5RcDNA that codes for membrane type IL-5R.

The surfaces of the pCAGGS.5R.8 transfected COS7 ($5 \times 10^6$) cells were labeled with $^{125}$I using Iodobeads (Pierce Chemical, Rockford, Ill.). The cell was disrupted and H7 antibody was added to the cell lysate. Protein G-Sepharose (Pharmacia, Piscataway, N.J.) was added to the mixture and the mixture was incubated at 4° C. for 12 hours. The proteins adsorbed on the Sepharose was loaded on the SDS-PAGE. After electrophoresis under a reducing condition, the gel was analyzed with Bio-Analyzer 100. The band (MW: about 60 KD) was found only in the lane where the sample was prepared from the cell transfected with pCAGGS.5R.8(FIG. 5).

Purification and Amino acid Sequence Analysis of Secretory IL-5R (Murine)

The IL-5R cDNA fragment obtained by XhoI digestion of pIL-5R.2 was inserted into pCAGGS vector by the similar method as in the case of pIL-5R.8 and the construct was designated as pCAGGS.5R.2. E. coli was transformed with the pCAGGS.5R.2 and the transformant was designated as E. coli 5R.2. E. coli 5R.2 was deposited with Fermentation Research Institute, Agency of Industrial Science and Technology, ministry of International Trade and Industry of 1-3, Higashi 1-chome, Tsukuba-shi, Ibaraki-ken, 305 Japan and was assigned the accession number FERM BP 3084.

COS7 cells were transfected with pCAGGS.5R.2 DNA according to the DEAE dextran method and was cultured in serum free medium (Iscove's DMEM) for two days. The culture supernatant was concentrated and the concentrate was electrophoresed on SDS-PAGE. A band (MW: approximately 50,000) was found in the lane on which the culture supernatant of pCAGGS.5R.2 transfected COS7 was loaded, while no band was found in the lane on which the culture supernatant of the pCAGGS vector alone was loaded. The culture supernatant of the pCAGGS.5R.2 transfected COS7 was loaded onto a column filled with H7 antibodies bound glycosylhard-gel (Seikagaku Kogyo, Tokyo). The column was washed with 2 mM HEPFS solution containing 0.1% CHAPS and then H7 bound fractions were eluted out with 350 mM acetic acid. The fractions were lyophilized and then solubilized in a sample buffer for SDS-PAGE. The mixture was electrophoresed according to the method described by Laemmli in Nature 227: 680, 1970. The protein on the gel was transferred to a polyvinylidene difluoride membrane (Millipore, Bedford, Mass.) according to the electroblotting method. The band corresponding to a molecular weight of about 50,000 was cut out of the membrane and analyzed with a gas phase sequencer 447A (with HPLC system, Applied Biosystem Co.). The amino acid sequence of the N terminus of secretory-IL-5R was as follows: Asp-Leu-Leu-Asn-His-Lys-Lys-Phe-Leu-Leu-Leu-Pro-Pro-Val-X-Phe-Thr-Ile-Lys-Ala. This amino acid sequence was found to be the same one (amino acid number 18–37) deduced from the nucleotide sequence of pIL-5R.8, membrane bound IL-5R cDNA clone. The amino acid sequence (amino acid number 1–17) is believed to be a signal peptide. X (amino acid number 15) may be Asn, which is deduced from the nucleotide sequence of cDNA, and to which a N-linked oligosaccharide is believed to bind.

The following Examples are described for human IL-5R.

Preparation of human Poly(A)$^+$ RNA

Eosinophils were obtained from 28 liter of peripheral blood of healthy volunteers and 50 ml of peripheral blood of a patient with eosinophilia. After removing erythrocytes, fractions containing eosinophils (1.09 g/ml) were collected from each sample by a density gradient centrifugation using Ficoll. The fraction contained 50% eosinophils and the number of eosinophis was $2.8 \times 10^9$ [healthy volunteers (helv)] and $2.0 \times 10^9$ [eosinophilia (eosi)]. 5 µg of poly(A)$^+$ RNA was recovered from each cell source as described above.

Construction of Human IL-5R cDNA Library

5 µg of each poly(A)$^+$ RNA thus obtained was used to synthesize cDNA (helv-cDNA, eosi-cDNA) as described above. The helv-cDNA was ligated to a BstXI linker and a fragment of helv-cDNA-linker complex having a size of 1,000 bp or more was selected. The fragment was then inserted into a BstXI digested pAGS-3 vector. E. coli MC1061 was transformed with the recombinant plasmid and about one million transformants were obtained (helv-cDNA library). The eosi-cDNA was ligated to a EcoRI linker and fragments of eosi-cDNA-linker complex having a size of 1,000 bp or more were selected. The fragments were inserted into a EcoRI digested λgt10 vector. E. coli C600Hfl was infected with the recombinant phage and 1.6 million independent plaques were obtained (eosi-cDNA library).

Screening of helv- and eosi-cDNA libraries according to the colony-hybridization method The helv-cDNA library was screened according to the colony hybridization method. One million colonies of the helv-cDNA library were grown on a solid medium and the colonies were transferred to 100 sheets of nitrocellulose membranes (8 cm in diameter). After DNA fixation, the membrane was placed in a bag containing 10× Denhardt's solution, 6 × SSC (0.9M NaCl, 0.09M sodium citrate), 100 μg/ml of heat-denatured salmon sperm DNA. The $^{32}$P-labeled, 1.2 kb HindIII-PstI fragment of pIL-5R.8 was added to the bag and hybridization was carried out at 65° C. for 24 hours under less stringent conditions. The membrane was washed at 45° C. in a solution containing 1× SSC and 0.1% SDS. After washing, a X-ray film was overlayed on the membrane for autoradiography as described above. A positive clone was obtained and was designated as ph5R.1. However, the cDNA fragment of ph5R.1 was found to contain only 1.0 kb, which was not an right size for IL-5R. Subsequently, the eosi-cDNA library was screened using the XhoI digested, 1.0 kb fragment of ph5R.1 as a probe according to the protocol of Colony/Plaque Screen. Approximately one million clones of the eosi-cDNA library was grown on a solid medium and the plaques were transferred to nylon membranes (13 cm in diameter, Colony/Plaque Screen, Dupont-NEN, Boston, Mass.). Hybridization was carried out at 65° C. for 24 hours in a solution containing 1% SDS, 1M NaCl, 10% Dextran sulfate, 100 μg/ml of heat-denatured salmon sperm DNA. After hybridization, the membrane was washed at 65° C. for an hour in a solution containing 2× SSC and 1% SDS. Two positive clones containing about 2 kb cDNA fragment were obtained and designated as HSIL5R and HSIL5R2.

E. coli was transformed with HSIL5R or HSIL5R2 and the transformants were designated as E. coli HSIL5R or E. coli HSIL5R2, respectively.

The transformants were deposited with Fermentation Research Institute, Agency of Industrial Science and Technology, ministry of International Trade and Industry of 1-3, Higashi 1-chome, Tsukuba-shi, Ibaraki-ken, 305 Japan and were assigned the accession number as follows:

|  | Accession No. |
| --- | --- |
| E. coli HSIL5R | FERM BP-3542 |
| E. coli HSIL5R2 | FERM BP-3543 |

DNA Sequence Analysis of HILS5R and HSIL5R2

HILS5R and HSIL5R2 were digested with EcoRI, and the EcoRI digested IL-5R fragment was inserted into the EcoRI site of Bluescript KS (−) vector (Stratagene, La Jolla, Calif.). The nucleotide sequence was determined according to the Sanger's method. The sequence was determined in both 5' and 3' direction. Initial primers were synthesized according to the sequence of the 5' upstream of the IL-5R cDNA fragment (T3 primer) and of the 3' downstream of the IL-5R cDNA fragment (T7 primer). After the 5' and 3' end sequences were determined, subsequent primers were synthesized according the sequence analyzed by the DNA sequencing. The nucleotide sequence thus determined was found to be complementary.

SEQ ID No. 17 shows the nucleotide and the corresponding amino acid sequence of HSIL5R. The first 20 amino acids are hypothetically a signal peptide and amino acids 345 to 365 are believed to be a transmembrane region according to hydropathy plot. These assumption are based on the same model as those of mouse. Amino acids 35–37, 131–133, 137–139, 142–144, 216–218, and 244–246 seem to be the sites of N-linked oligosaccharide addition. The estimated molecular weight (45,556) of IL-5R from cDNA clone differs from the real molecular weight (about 60,000) of IL-5R produced by the transformed COS7 cell. The difference of the weight may be due to the N-linked oligosaccharide. The nucleotide sequence downstream of nucleotide position 1245 distinguishes HSIL5R (SEQ ID No.17) from HSIL5R2(SEQ ID No.18).

SEQ ID No.18 shows the nucleotide and the corresponding amino acid sequence of HSIL5R2. The amino acid sequence of HSIL5R2 terminates at Ile (amino acid number 396), while HSIL5R contains additional 24 amino acids following Ser at amino acid No. 396. The amino acid sequences of HSIL5R and HSIL5R2 are identical from Met (amino acid number 1) to Gly (amino acid number 395) except for an amino acid at position 129 where the amino acid is Val on the sequence of HSIL5 and Ile on the sequence of HSIL5R2.

Expression of human IL-5R on COS7 and Cross-linking experiment

The Bluescript kS (−) recombinant was digested with EcoRI. The restriction fragments containing IL-5R of HSIL5R and HSIL5R2 were inserted into pCAGGS. The resulting constructs were designated as pCAGGS.HSIL-5R and pCAGGS.HSIL5R2. COS7 cells were transfected with these recombinant DNAs and the transformed cells were tested for their chemical characteristics using $^{35}$S-labeled murine IL-5 or $^{125}$I-labeled human IL-5 (2×10$^6$ cpm/μg) according to the cross-linking method.

Figure 7:
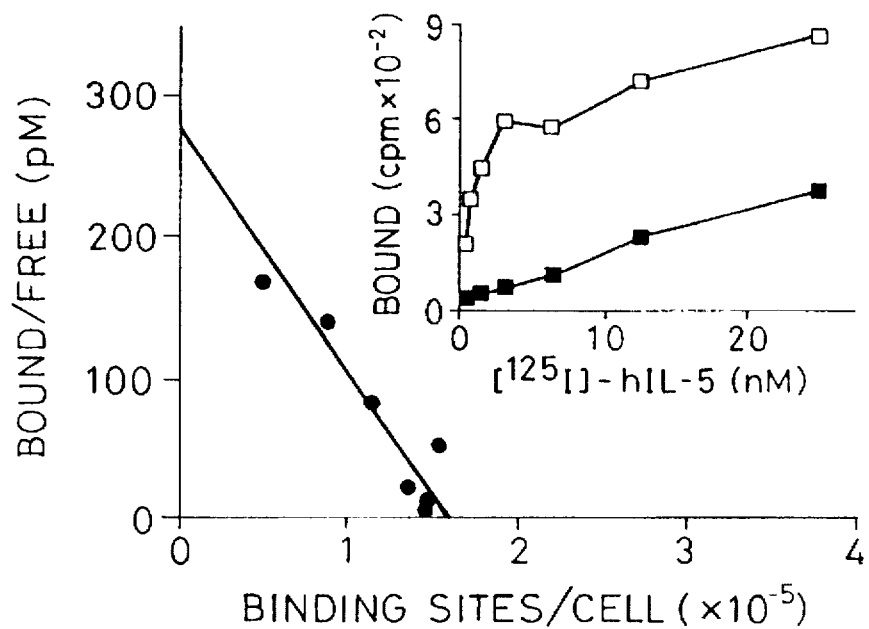
FIG. 7A–7D shows Scatchard plot analyses of a binding assay of $^{35}$S-labeled murine IL-5 or $^{125}$I labeled human IL-5 to the pCAGGS.HSIL5R or pCAGGS.HSIL5R2 transfected COS 7 cell. The symbol □ represents a total binding and the symbol ■ represents a nonspecific binding in the presence of a 100-fold excess of non-radiolabeled IL-5. COS 7 cells were transfected with pCAGGS.HSIL5R and the transformant was tested for binding using $^{125}$I-labeled human IL-5 (FIG. 7A, inset of FIG. 7A). COS 7 cells were transfected with pCAGGS.HSIL5R2 and the transformant was tested for binding using $^{125}$I-labeled human IL-5 (FIG. 7B, inset of FIG. 7B). COS 7 cells were transfected with pCAGGS.HSIL5R and the transformant was tested for binding using $^{35}$S-labeled mouse IL-5 (FIG. 7C, inset of FIG. 7C). COS 7 cells were transfected with pCAGGS.HSIL5R2 and the transformant was tested for binding using $^{35}$S-labeled mouse IL-5 (FIG. 7D, inset of FIG. 7D).
Figure 7:
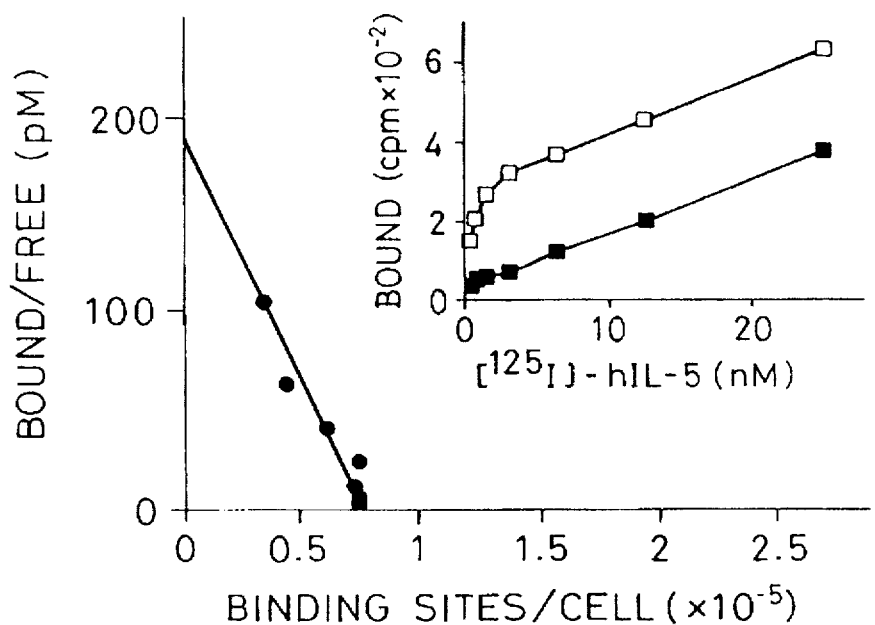
Figure 7:
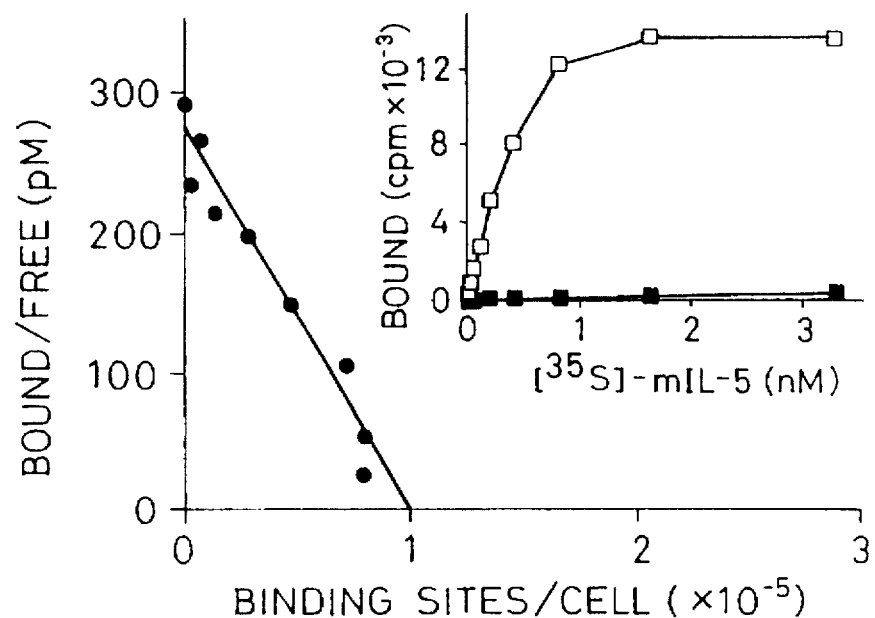
Figure 7:
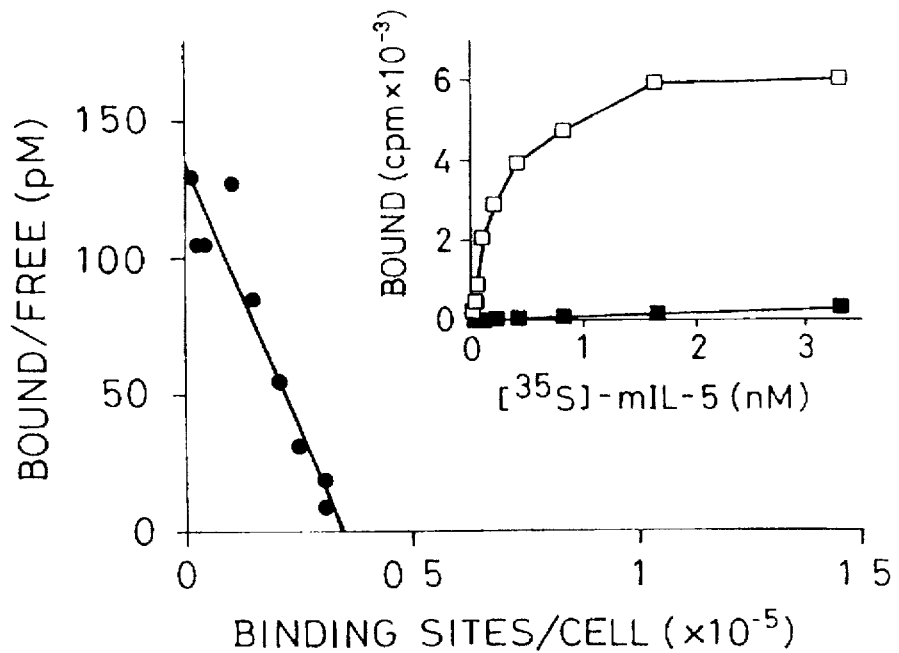

Binding of $^{125}$I-labeled human IL-5 to IL-5R expressed on the COS7 cell (pCAGGS.HSIL5R transformant) was shown in the inset of FIG. 7A, and the results analyzed by Scatchard plot was shown in FIG. 7A. Binding of $^{125}$I-labeled human IL-5 to IL-5R expressed on COS7 cell (pCAGGS.HSIL5R2 transformant) was shown in the inset of FIG. 7B, and the results analyzed by Scatchard plot was shown in FIG. 7B. Binding of $^{35}$S-labeled murine IL-5 to IL-5R expressed on the COS7 cells (pCAGGS.HSIL5R transformant) was shown in the inset of FIG. 7C, and the results analyzed by Scatchard plot was shown in FIG. 7C. Binding of $^{35}$S-labeled murine IL-5 to IL-5R expressed on COS7 cell (pCAGGS.HSIL5R2 transformant) was shown in the inset of FIG. 7D, and the results analyzed by Scatchard plot were shown in FIG. 7D.

A high affinity IL-5R with the dissociation constant ($K_D$) of less than 100 pM was not detectable by $^{125}$I-labeled human IL-5 because of poor specific radioactivity. To calculate the dissociation constant of a high affinity IL-5R, we used $^{35}$S-labeled mouse IL-5 which has high specific radioactivity and is not denatured. The dissociation constant of the pCAGGS.HSIL5R transfected COS7 cells were about 590 pM when radiolabeled human IL-5 was used, while the dissociation constant of the same pCAGGS.HS IL5R transfected COS7 cells were about 250 pM when radiolabeled mouse IL-5 was used. The dissociation constant of the pCAGGS.HSIL5R2 transfected COS7 cells were about 410 pM with radiolabeled human IL-5, while the dissociation constant of the same pCAGGS.HSIL5R2 transfected COS7 cells were about 355 pM when radiolabeled mouse IL-5 was used. These results are comparable to the dissociation constant (170–330 pM) of eosinophils from healthy adult peripheral blood that we reported previously. The data of the previous report were calculated by Scatchard analysis of binding assays using $^{35}$S-labeled mouse IL-5.

The dissociation constant thus determined was higher than that of mouse low affinity IL-5R and fell into the average value of normal human eosinophils. Taken altogether, the isolated IL-5R cDNA fragment was expressed on the surface of the COS7 cells and the IL-5R expressed on the cell surface are responsible for the binding of human IL-5.

Figure 8:
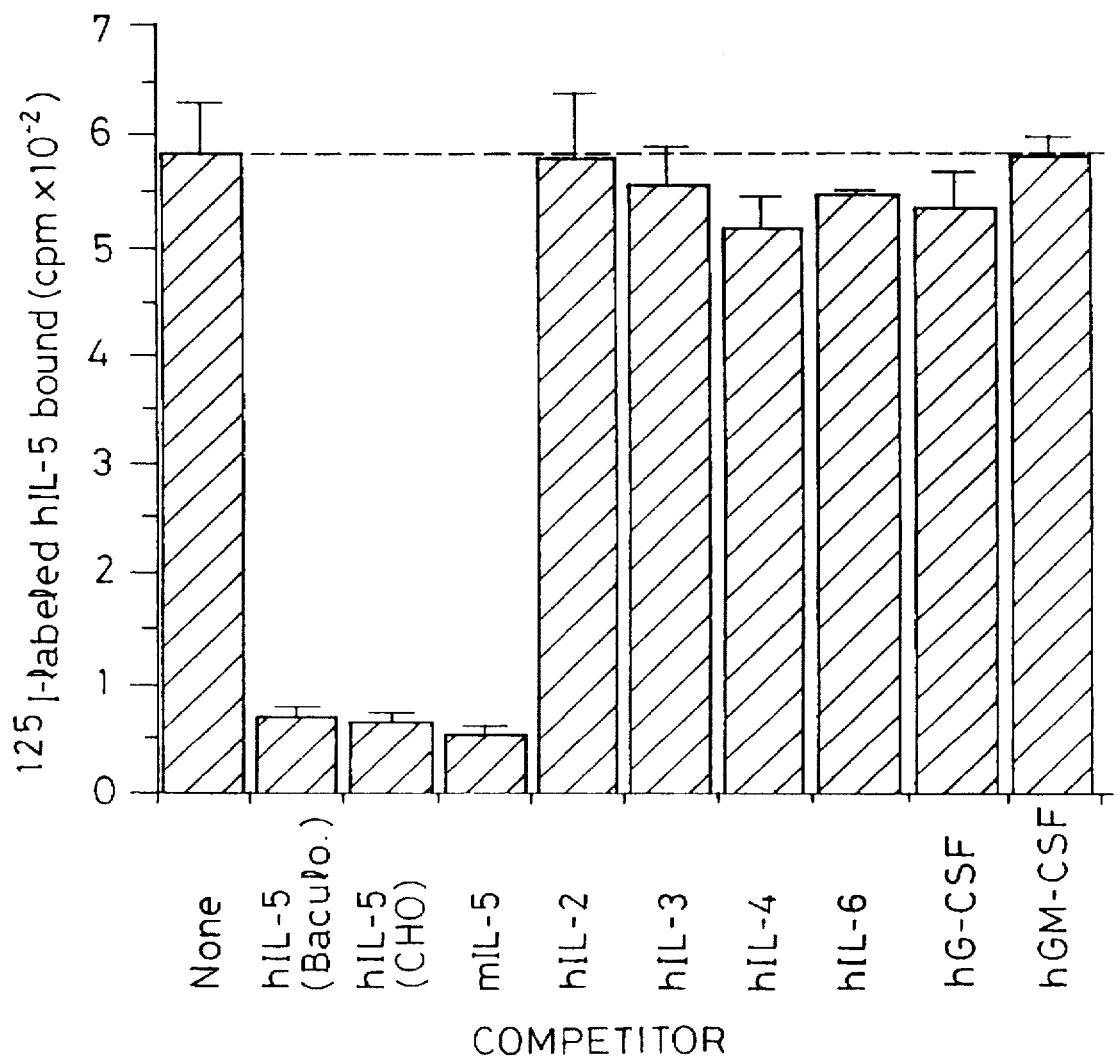
FIG. 8 is a bar graph showing the binding specificity of $^{125}$I labeled human IL-5 to IL-5R. 100 μl of the COS 7 transformants ($4\times10^5$ cells) carrying pCAGGS.HSIL5R and 500 pM $^{125}$I-labeled human IL-5 were incubated in the presence of a 1,000-fold excess of cytokines.

FIG. 8 shows inhibitory effects of cytokines on the binding of IL-5 to IL-5R. IL-5R expressed on the COS7 transformants specifically binds to human and mouse IL-5 but not to human IL-2, human IL-3, human IL-4, human IL-6, human GM-CSF or human G-CSF.

Cross-linking of Radiolabeled IL-5 to the COS7 Transformants

The COS7 transformant ($1\times10^5$ cells) carrying pCAGGS.HSIL5R or pCAGGS.HSIL5R2 and either 5.5 nM $^{35}$S-labeled mouse IL-5 or 1 nM $^{125}$I-labeled human IL-5 were mixed in the presence or absence of 250-fold excess of non-labeled IL-5. After one hour incubation at 4° C., 1 mM bis(sulfosuccinimidyl) suberate (Pierce Chemical Co., Rockford, Ill.) was added to the mixture. The mixture was further incubated at 4° C. for 30 minutes. After the incubation, binding was analyzed as described above.

Figure 9:
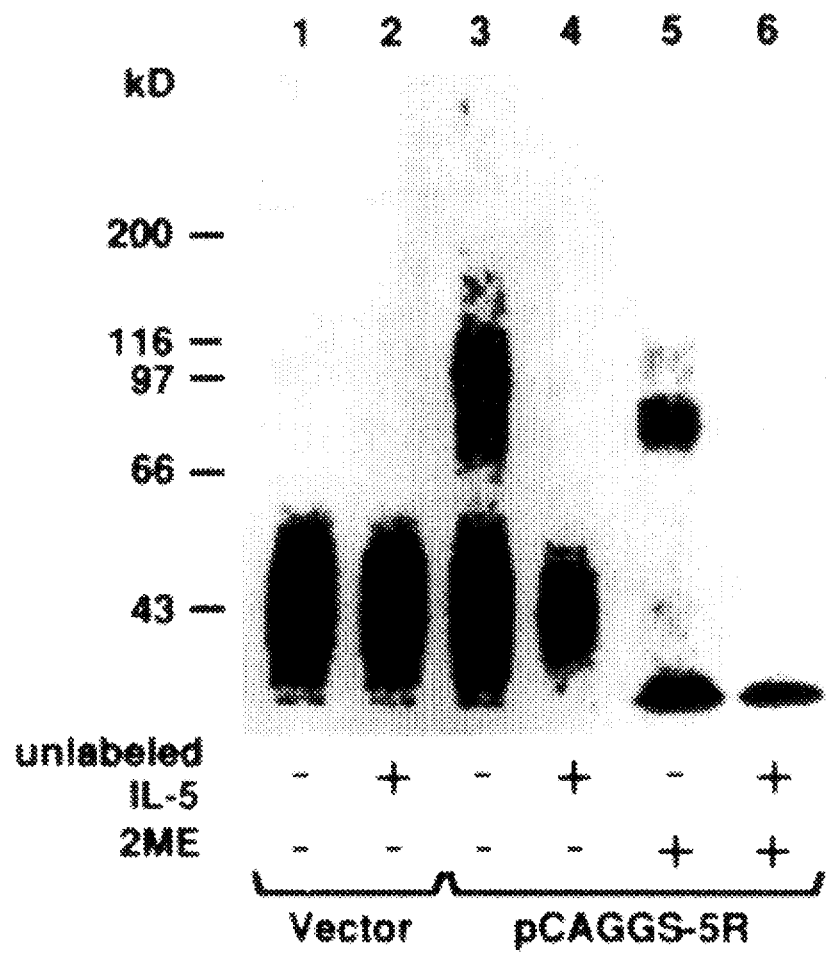
FIG. 9 shows a band pattern of chemical cross-linking of IL-5 analysed by SDS-PAGE. COS cells were transfected with a pCAGGS vector and the transformant was incubated with $^{35}$S-labeled murine IL-5 (lane 1) or $^{125}$I-labeled human IL-5 (lane 4). Then a cross-linking agent, bis (sulfosuccinimidyl) suberate was added to the mixture. After incubation, the mixture was electrophoresed under non-reduced condition. Similarly, COS7 cells were transfected with pCAGGS. HSIL5R and the transformants were incubated with $^{35}$S-labeled murine IL-5 in the presence (lane 3) or absence (lane 2) of an excess amount of non-labeled murine IL-5 or with $^{125}$I-labeled human IL-5 in the presence (lane 6) or absence (lane 5) of an excess amount of non-labeled human IL-5. Then, a cross-linking agent, bis (sulfosuccinimidyl) suberate was added to the mixture. After incubation, the mixture was electrophoresed under non-reducing condition.

In FIG. 9, COS7 cells transfected with a pCAGGS vector alone or pCAGGSHSIL5R were incubated with $^{35}$S-labeled murine IL-5 (A; lane 1, 2, 3) or $^{125}$I-labeled human IL-5(B; lane 4, 5, 6). COS7 cells transfected with a pCAGGS.HSIL5R were incubated with $^{35}$S-labeled murine IL-5 in the presence (lane 3) or absence (lane 2) of 250-fold excess of non-labeled IL-5, or were incubated with $^{125}$I-labeled human IL-5 in the presence (lane 6) or absence (lane 5) of 250-fold excess amount of non-labeled IL-5.

There were two bands corresponding to about 105 kD (lane 2) and 86 kD (lane 5). Since murine IL-5 is 45 kD and human IL-5 is 31 kD, the molecular weight of human IL-5R could be estimated to be 55,000–60,000. This molecular weight of human IL-5R is almost the same as that of IL-5R expressed on eosinophils as we reported previously (Cellular Immunology, 133; 484–469). In the presence of a 250-fold excess of non-labeled IL-5, no band was found (lanes 3, 6 in FIG. 9).

Same experiment was carried out using pCAGGS.HSIL5R2 and the results were very similar to that described above.

---

What is claimed is:

1. An isolated cDNA sequence coding for murine interleukin 5 receptor wherein the amino acid sequence of the interleukin 5 receptor comprises the sequence described in SEQ ID NO. 5 6, 7, or 8.

2. The isolated cDNA sequence of claim 1 wherein the nucleotide sequence comprises the sequence described in SEQ ID NO.1.

3. The isolated cDNA sequence of claim 1 wherein the nucleotide sequence comprises the sequence described in SEQ ID NO.2.

4. An isolated cDNA sequence of claim 1 wherein said murine interleukin 5 receptor is a secretory murine interleukin 5 receptor.

5. The isolated cDNA sequence of claim 4 wherein the nucleotide sequence comprises the sequence described in SEQ ID NO.3.

6. The isolated cDNA sequence of claim 4 wherein the nucleotide sequence comprises the sequence described in SEQ ID NO.4.

7. An isolated DNA sequence capable of hybridizing with the complement of the cDNA described in SEQ ID NO. 1, 2, 3, or 4 under stringent condition and which codes for a protein having binding specificity for murine interleukin 5.

8. A COS monkey cell transfected with a recombinant vector containing the cDNA sequence of any one of claims 1–6.

9. A method of producing a murine interleukin 5 receptor having an amino acid sequence comprising the sequence described in SEQ ID NO. 5, 6, 7, or 8, which comprises culturing a cell capable of expressing the murine interleukin 5 receptor in a medium and isolating the murine interleukin 5 receptor from the cell or the culture supernatant using an interleukin 5 receptor antibody.

10. A method of producing a murine interleukin 5 receptor having an amino acid sequence comprising the sequence described in SEQ ID NO. 5, 6, 7, or 8, which comprises culturing the COS cell of claim 8 in a medium, and recovering the murine interleukin 5 receptor from the culture supernatant.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 1245 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
ATGGTGCCTG   TGTTACTAAT   TCTTGTGGGA   GCTTTGGCAA   CACTGCAAGC   TGACTTACTT       60

AATCACAAAA   AGTTTTTACT   TCTACCACCT   GTCAATTTTA   CCATTAAAGC   CACTGGATTA      120

GCTCAAGTTC   TTTTACACTG   GGACCCAAAT   CCTGACCAAG   AGCAAAGGCA   TGTTGATCTA      180

GAGTATCACG   TGAAAATAAA   TGCCCCACAA   GAAGACGAAT   ATGATACCAG   AAAGACTGAA      240

AGCAAATGTG   TGACCCCCCT   TCATGAAGGC   TTTGCAGCTA   GCGTGAGGAC   CATTCTGAAG      300

AGCAGCCATA   CAACTCTGGC   CAGCAGTTGG   GTTTCTGCTG   AACTCAAAGC   TCCACCAGGA      360

TCTCCTGGAA   CCTCGGTTAC   GAATTTAACT   TGTACCACAC   ACACTGTTGT   AAGTAGCCAC      420

ACCCACTTAA   GGCCATACCA   AGTGTCCCTT   CGTTGCACCT   GGCTTGTTGG   GAAGGATGCC      480

CCTGAGGACA   CACAGTATTT   CCTATACTAC   AGGTTTGGTG   TTTTGACTGA   AAAATGCCAA      540

GAATACAGCA   GAGATGCACT   GAACAGAAAT   ACTGCATGCT   GGTTTCCCAG   GACATTTATC      600

AACAGCAAAG   GGTTTGAACA   GCTTGCTGTG   CACATTAATG   GCTCAAGCAA   GCGTGCTGCA      660

ATCAAGCCCT   TTGATCAGCT   GTTCAGTCCA   CTTGCCATTG   ACCAAGTGAA   TCCTCCAAGG      720

AATGTCACAG   TGGAAATTGA   AAGCAATTCT   CTCTATATAC   AGTGGGAGAA   ACCACTTTCT      780

GCCTTTCCAG   ATCATTGCTT   TAACTATGAG   CTGAAAATTT   ACAACACAAA   AAATGGTCAC      840

ATTCAGAAGG   AAAAACTGAT   CGCCAATAAG   TTCATCTCAA   AAATTGATGA   TGTTTCTACA      900
```

```
TATTCCATTC  AAGTGAGAGC  AGCTGTGAGC  TCACCTTGCA  GAATGCCAGG  AAGGTGGGGC      960

GAGTGGAGTC  AACCTATTTA  TGTGGGAAAG  GAAAGGAAGT  CCTTGGTAGA  ATGGCATCTC     1020

ATTGTGCTCC  CAACAGCTGC  CTGCTTCGTC  TTGTTAATCT  TCTCACTCAT  CTGCAGAGTG     1080

TGTCATTTAT  GGACCAGGTT  GTTCCACCG   GTTCCGGCCC  CAAAGAGTAA  CATCAAAGAT     1140

CTCCCTGTGG  TTACTGAATA  TGAGAAACCT  TCGAATGAAA  CCAAAATTGA  AGTTGTACAT     1200

TGTGTGGAAG  AGGTTGGATT  TGAAGTCATG  GGAAATTCCA  CGTTT                     1245
```

( 2 ) INFORMATION FOR SEQ ID NO:2:

( i ) SEQUENCE CHARACTERISTICS:
        ( A ) LENGTH: 1808 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
GAAATAATTG  GTAAACACAG  AAAATGTTTC  AATAGAAAAA  AGAGGAAACA  GAACACTGTG       60

TAGCCCTGTT  ATCAGCAGAG  ACAGAGCTAA  CGCTGGGGAT  ACCAAACTAG  AAGAAGCTCA      120

CTGGACAGGT  CCCGGTATGC  AGTTCTATTT  TTGTTGATGG  CTCTGTATCT  AATGTGTTCA      180

TTTGTACCAA  GGATCTAACC  AGGGTCTTCC  AGAGTCTGAG  CAAGCTTCTC  CCACTGAGCT      240

ACATCACAGC  CCCCTGTTTA  TTGGAAGAAG  AAATACTTAC  ACCTTTCCAG  TATTCGGCTA      300

CCATGGTGCC  TGTGTTACTA  ATTCTTGTGG  GAGCTTTGGC  AACACTGCAA  GCTGACTTAC      360

TTAATCACAA  AAAGTTTTTA  CTTCTACCAC  CTGTCAATTT  TACCATTAAA  GCCACTGGAT      420

TAGCTCAAGT  TCTTTTACAC  TGGGACCCAA  ATCCTGACCA  AGAGCAAAGG  CATGTTGATC      480

TAGAGTATCA  CGTGAAAATA  AATGCCCCAC  AAGAAGACGA  ATATGATACC  AGAAAGACTG      540

AAAGCAAATG  TGTGACCCCC  CTTCATGAAG  GCTTTGCAGC  TAGCGTGAGG  ACCATTCTGA      600

AGAGCAGCCA  TACAACTCTG  GCCAGCAGTT  GGGTTTCTGC  TGAACTCAAA  GCTCCACCAG      660

GATCTCCTGG  AACCTCGGTT  ACGAATTTAA  CTTGTACCAC  ACACACTGTT  GTAAGTAGCC      720

ACACCCACTT  AAGGCCATAC  CAAGTGTCCC  TTCGTTGCAC  CTGGCTTGTT  GGGAAGGATG      780

CCCCTGAGGA  CACACAGTAT  TTCCTATACT  ACAGGTTTGG  TGTTTTGACT  GAAAAATGCC      840

AAGAATACAG  CAGAGATGCA  CTGAACAGAA  ATACTGCATG  CTGGTTTCCC  AGGACATTTA      900

TCAACAGCAA  AGGGTTTGAA  CAGCTTGCTG  TGCACATTAA  TGGCTCAAGC  AAGCGTGCTG      960

CAATCAAGCC  CTTTGATCAG  CTGTTCAGTC  CACTTGCCAT  TGACCAAGTG  AATCCTCCAA     1020

GGAATGTCAC  AGTGGAAATT  GAAAGCAATT  CTCTCTATAT  ACAGTGGGAG  AAACCACTTT     1080

CTGCCTTTCC  AGATCATTGC  TTTAACTATG  AGCTGAAAAT  TTACAACACA  AAAAATGGTC     1140

ACATTCAGAA  GGAAAAACTG  ATCGCCAATA  AGTTCATCTC  AAAAATTGAT  GATGTTTCTA     1200

CATATTCCAT  TCAAGTGAGA  GCAGCTGTGA  GCTCACCTTG  CAGAATGCCA  GGAAGGTGGG     1260

GCGAGTGGAG  TCAACCTATT  TATGTGGGAA  AGGAAAGGAA  GTCCTTGGTA  GAATGGCATC     1320

TCATTGTGCT  CCCAACAGCT  GCCTGCTTCG  TCTTGTTAAT  CTTCTCACTC  ATCTGCAGAG     1380

TGTGTCATTT  ATGGACCAGG  TTGTTCCAC   CGGTTCCGGC  CCAAAGAGT   AACATCAAAG     1440

ATCTCCCTGT  GGTTACTGAA  TATGAGAAAC  CTTCGAATGA  AACCAAAATT  GAAGTTGTAC     1500

ATTGTGTGGA  AGAGGTTGGA  TTTGAAGTCA  TGGGAAATTC  CACGTTTTGA  TGGCATTTTG     1560

CCATTCTGAA  ATGAACTCAT  ACAGGACTCC  GTGATAAGAG  CAAGGACTGC  TATTTCTTGG     1620

CAAGGAGGTA  TTTCAAATGA  ACACTCAGAG  CCAGGCGGTG  GTAGAGCTCG  CCTTTAATAC     1680
```

-continued

| | | | | | |
|---|---|---|---|---|---|
|CAGCACCTGG|GATGCACAGA|CGGGAGGATT|TCTGAGTTCG|AGGCCAGCTT|GGTCTATAAA 1740|
|GTGAGTTCCA|GGACAGCCAG|AGCTACACAG|AGAAACCCTG|TCTCGAAAAA|ACAAACAAAC 1800|
|AAACAAAC|||||1808|

( 2 ) INFORMATION FOR SEQ ID NO:3:

( i ) SEQUENCE CHARACTERISTICS:
        ( A ) LENGTH: 996 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

| | | | | | |
|---|---|---|---|---|---|
|ATGGTGCCTG|TGTTACTAAT|TCTTGTGGGA|GCTTTGGCAA|CACTGCAAGC|TGACTTACTT 60|
|AATCACAAAA|AGTTTTTACT|TCTACCACCT|GTCAATTTTA|CCATTAAAGC|CACTGGATTA 120|
|GCTCAAGTTC|TTTTACACTG|GGACCCAAAT|CCTGACCAAG|AGCAAAGGCA|TGTTGATCTA 180|
|GAGTATCACG|TGAAAATAAA|TGCCCCACAA|GAAGACGAAT|ATGATACCAG|AAAGACTGAA 240|
|AGCAAATGTG|TGACCCCCCT|TCATGAAGGC|TTTGCAGCTA|GCGTGAGGAC|CATTCTGAAG 300|
|AGCAGCCATA|CAACTCTGGC|CAGCAGTTGG|GTTCTGCTG|AACTCAAAGC|TCCACCAGGA 360|
|TCTCCTGGAA|CCTCGGTTAC|GAATTTAACT|TGTACCACAC|ACACTGTTGT|AAGTAGCCAC 420|
|ACCCACTTAA|GGCCATACCA|AGTGTCCCTT|CGTTGCACCT|GGCTTGTTGG|GAAGGATGCC 480|
|CCTGAGGACA|CACAGTATTT|CCTATACTAC|AGGTTTGGTG|TTTGACTGA|AAAATGCCAA 540|
|GAATACAGCA|GAGATGCACT|GAACAGAAAT|ACTGCATGCT|GGTTTCCCAG|GACATTTATC 600|
|AACAGCAAAG|GGTTTGAACA|GCTTGCTGTG|CACATTAATG|GCTCAAGCAA|GCGTGCTGCA 660|
|ATCAAGCCCT|TTGATCAGCT|GTTCAGTCCA|CTTGCCATTG|ACCAAGTGAA|TCCTCCAAGG 720|
|AATGTCACAG|TGGAAATTGA|AAGCAATTCT|CTCTATATAC|AGTGGGAGAA|ACCACTTTCT 780|
|GCCTTTCCAG|ATCATTGCTT|TAACTATGAG|CTGAAAATTT|ACAACACAAA|AAATGGTCAC 840|
|ATTCAGAAGG|AAAAACTGAT|CGCCAATAAG|TTCATCTCAA|AAATTGATGA|TGTTTCTACA 900|
|TATTCCATTC|AAGTGAGAGC|AGCTGTGAGC|TCACCTTGCA|GAATGCCAGG|AAGGTGGGGC 960|
|GAGTGGAGTC|AACCTATTTA|TGTGGAAACC|TTCGAA|||996|

( 2 ) INFORMATION FOR SEQ ID NO:4:

( i ) SEQUENCE CHARACTERISTICS:
        ( A ) LENGTH: 1355 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

| | | | | | |
|---|---|---|---|---|---|
|TATTCGGCTA|CCATGGTGCC|TGTGTTACTA|ATTCTTGTGG|GAGCTTTGGC|AACACTGCAA 60|
|GCTGACTTAC|TTAATCACAA|AAAGTTTTTA|CTTCTACCAC|CTGTCAATTT|TACCATTAAA 120|
|GCCACTGGAT|TAGCTCAAGT|TCTTTTACAC|TGGGACCCAA|ATCCTGACCA|AGAGCAAAGG 180|
|CATGTTGATC|TAGAGTATCA|CGTGAAAATA|AATGCCCCAC|AAGAAGACGA|ATATGATACC 240|
|AGAAAGACTG|AAAGCAAATG|TGTGACCCCC|CTTCATGAAG|GCTTTGCAGC|TAGCGTGAGG 300|
|ACCATTCTGA|AGAGCAGCCA|TACAACTCTG|GCCAGCAGTT|GGGTTCTGC|TGAACTCAAA 360|
|GCTCCACCAG|GATCTCCTGG|AACCTCGGTT|ACGAATTTAA|CTTGTACCAC|ACACACTGTT 420|

-continued

```
GTAAGTAGCC ACACCCACTT AAGGCCATAC CAAGTGTCCC TTCGTTGCAC CTGGCTTGTT        480
GGGAAGGATG CCCCTGAGGA CACACAGTAT TTCCTATACT ACAGGTTTGG TGTTTTGACT        540
GAAAAATGCC AAGAATACAG CAGAGATGCA CTGAACAGAA ATACTGCATG CTGGTTTCCC        600
AGGACATTTA TCAACAGCAA AGGGTTTGAA CAGCTTGCTG TGCACATTAA TGGCTCAAGC        660
AAGCGTGCTG CAATCAAGCC CTTTGATCAG CTGTTCAGTC CACTTGCCAT TGACCAAGTG        720
AATCCTCCAA GGAATGTCAC AGTGGAAATT GAAAGCAATT CTCTCTATAT ACAGTGGGAG        780
AAACCACTTT CTGCCTTTCC AGATCATTGC TTTAACTATG AGCTGAAAAT TTACAACACA        840
AAAAATGGTC ACATTCAGAA GGAAAAACTG ATCGCCAATA AGTTCATCTC AAAAATTGAT        900
GATGTTTCTA CATATTCCAT TCAAGTGAGA GCAGCTGTGA GCTCACCTTG CAGAATGCCA        960
GGAAGGTGGG GCGAGTGGAG TCAACCTATT TATGTGAAA CCTTCGAATG AAACCAAAAT       1020
TGAAGTTGTA CATTGTGTGG AAGAGGTTGG ATTTGAAGTC ATGGGAAATT CCACGTTTTG       1080
ATGGCATTTT GCCATTCTGA AATGAACTCA TACAGGACTC CGTGATAAGA GCAAGGACTG       1140
CTATTTCTTG GCAAGGAGGT ATTTCAAATG AACACTCAGA GCCAGGCGGT GGTAGAGCTC       1200
GCCTTTAATA CCAGCACCTG GGATGCACAG ACGGGAGGAT TTCTGAGTTC GAGGCCAGCT       1260
TGGTCTATAA AGTGAGTTCC AGGACAGCCA GAGCTACACA GAGAAACCCT GTCTCGAAAA       1320
AACAAACAAA CAAACAAACA AACAAAAATG AACAC                                  1355
```

(2) INFORMATION FOR SEQ ID NO:5:

(i) SEQUENCE CHARACTERISTICS:
      (A) LENGTH: 415 amino acids
      (B) TYPE: amino acid
      (C) STRANDEDNESS: unknown
      (D) TOPOLOGY: linear (ii) MOLECULE TYPE: peptide (xi) SEQUENCE DESCRIPTION: SEQ ID NO:5:

```
Met Val Pro Val Leu Leu Ile Leu Val Gly Ala Leu Ala Thr Leu Gln
  1               5                  10                  15

Ala Asp Leu Leu Asn His Lys Lys Phe Leu Leu Pro Pro Val Asn
             20                  25                  30

Phe Thr Ile Lys Ala Thr Gly Leu Ala Gln Val Leu Leu His Trp Asp
         35                  40                  45

Pro Asn Pro Asp Gln Glu Gln Arg His Val Asp Leu Glu Tyr His Val
     50                  55                  60

Lys Ile Asn Ala Pro Gln Glu Asp Glu Tyr Asp Thr Arg Lys Thr Glu
 65                  70                  75                  80

Ser Lys Cys Val Thr Pro Leu His Glu Gly Phe Ala Ala Ser Val Arg
                 85                  90                  95

Thr Ile Leu Lys Ser Ser His Thr Thr Leu Ala Ser Ser Trp Val Ser
                100                 105                 110

Ala Glu Leu Lys Ala Pro Pro Gly Ser Pro Gly Thr Ser Val Thr Asn
            115                 120                 125

Leu Thr Cys Thr Thr His Thr Val Val Ser Ser His Thr His Leu Arg
        130                 135                 140

Pro Tyr Gln Val Ser Leu Arg Cys Thr Trp Leu Val Gly Lys Asp Ala
145                 150                 155                 160

Pro Glu Asp Thr Gln Tyr Phe Leu Tyr Tyr Arg Phe Gly Val Leu Thr
                165                 170                 175

Glu Lys Cys Gln Glu Tyr Ser Arg Asp Ala Leu Asn Arg Asn Thr Ala
```

-continued

```
                    180                           185                           190

Cys Trp Phe Pro Arg Thr Phe Ile Asn Ser Lys Gly Phe Glu Gln Leu
                195                 200                 205

Ala Val His Ile Asn Gly Ser Ser Lys Arg Ala Ala Ile Lys Pro Phe
                210                 215                 220

Asp Gln Leu Phe Ser Pro Leu Ala Ile Asp Gln Val Asn Pro Pro Arg
        225                 230                 235                     240

Asn Val Thr Val Glu Ile Glu Ser Asn Ser Leu Tyr Ile Gln Trp Glu
                        245                 250                 255

Lys Pro Leu Ser Ala Phe Pro Asp His Cys Phe Asn Tyr Glu Leu Lys
                    260                 265                 270

Ile Tyr Asn Thr Lys Asn Gly His Ile Gln Lys Glu Lys Leu Ile Ala
                275                 280                 285

Asn Lys Phe Ile Ser Lys Ile Asp Asp Val Ser Thr Tyr Ser Ile Gln
                290                 295                 300

Val Arg Ala Ala Val Ser Ser Pro Cys Arg Met Pro Gly Arg Trp Gly
        305                 310                 315                     320

Glu Trp Ser Gln Pro Ile Tyr Val Gly Lys Glu Arg Lys Ser Leu Val
                        325                 330                 335

Glu Trp His Leu Ile Val Leu Pro Thr Ala Ala Cys Phe Val Leu Leu
                    340                 345                 350

Ile Phe Ser Leu Ile Cys Arg Val Cys His Leu Trp Thr Arg Leu Phe
                355                 360                 365

Pro Pro Val Pro Ala Pro Lys Ser Asn Ile Lys Asp Leu Pro Val Val
            370                 375                 380

Thr Glu Tyr Glu Lys Pro Ser Asn Glu Thr Lys Ile Glu Val Val His
        385                 390                 395                     400

Cys Val Glu Glu Val Gly Phe Glu Val Met Gly Asn Ser Thr Phe
                        405                 410                 415
```

( 2 ) INFORMATION FOR SEQ ID NO:6:

( i ) SEQUENCE CHARACTERISTICS:
        ( A ) LENGTH: 398 amino acids
        ( B ) TYPE: amino acid
        ( C ) STRANDEDNESS: unknown
        ( D ) TOPOLOGY: linear ( i i ) MOLECULE TYPE: peptide ( x i ) SEQUENCE DESCRIPTION: SEQ ID NO:6:

```
        Asp Leu Leu Asn His Lys Lys Phe Leu Leu Pro Pro Val Asn Phe
        1                   5                   10                  15

Thr Ile Lys Ala Thr Gly Leu Ala Gln Val Leu Leu His Trp Asp Pro
                        20                  25                  30

Asn Pro Asp Gln Glu Gln Arg His Val Asp Leu Glu Tyr His Val Lys
                    35                  40                  45

Ile Asn Ala Pro Gln Glu Asp Glu Tyr Asp Thr Arg Lys Thr Glu Ser
                50                  55                  60

Lys Cys Val Thr Pro Leu His Glu Gly Phe Ala Ala Ser Val Arg Thr
        65                  70                  75                  80

Ile Leu Lys Ser Ser His Thr Thr Leu Ala Ser Ser Trp Val Ser Ala
                        85                  90                  95

Glu Leu Lys Ala Pro Pro Gly Ser Pro Gly Thr Ser Val Thr Asn Leu
                    100                 105                 110

Thr Cys Thr Thr His Thr Val Val Ser Ser His Thr His Leu Arg Pro
                115                 120                 125
```

```
Tyr  Gln  Val  Ser  Leu  Arg  Cys  Thr  Trp  Leu  Val  Gly  Lys  Asp  Ala  Pro
     130                 135                 140

Glu  Asp  Thr  Gln  Tyr  Phe  Leu  Tyr  Tyr  Arg  Phe  Gly  Val  Leu  Thr  Glu
145                      150                 155                           160

Lys  Cys  Gln  Glu  Tyr  Ser  Arg  Asp  Ala  Leu  Asn  Arg  Asn  Thr  Ala  Cys
                    165                      170                      175

Trp  Phe  Pro  Arg  Thr  Phe  Ile  Asn  Ser  Lys  Gly  Phe  Glu  Gln  Leu  Ala
               180                 185                      190

Val  His  Ile  Asn  Gly  Ser  Ser  Lys  Arg  Ala  Ala  Ile  Lys  Pro  Phe  Asp
          195                 200                      205

Gln  Leu  Phe  Ser  Pro  Leu  Ala  Ile  Asp  Gln  Val  Asn  Pro  Pro  Arg  Asn
     210                      215                      220

Val  Thr  Val  Glu  Ile  Glu  Ser  Asn  Ser  Leu  Tyr  Ile  Gln  Trp  Glu  Lys
225                      230                 235                           240

Pro  Leu  Ser  Ala  Phe  Pro  Asp  His  Cys  Phe  Asn  Tyr  Glu  Leu  Lys  Ile
               245                      250                      255

Tyr  Asn  Thr  Lys  Asn  Gly  His  Ile  Gln  Lys  Glu  Lys  Leu  Ile  Ala  Asn
               260                 265                      270

Lys  Phe  Ile  Ser  Lys  Ile  Asp  Asp  Val  Ser  Thr  Tyr  Ser  Ile  Gln  Val
          275                 280                      285

Arg  Ala  Ala  Val  Ser  Ser  Pro  Cys  Arg  Met  Pro  Gly  Arg  Trp  Gly  Glu
     290                      295                 300

Trp  Ser  Gln  Pro  Ile  Tyr  Val  Gly  Lys  Glu  Arg  Lys  Ser  Leu  Val  Glu
305                      310                 315                           320

Trp  His  Leu  Ile  Val  Leu  Pro  Thr  Ala  Ala  Cys  Phe  Val  Leu  Leu  Ile
               325                      330                           335

Phe  Ser  Leu  Ile  Cys  Arg  Val  Cys  His  Leu  Trp  Thr  Arg  Leu  Phe  Pro
               340                 345                      350

Pro  Val  Pro  Ala  Pro  Lys  Ser  Asn  Ile  Lys  Asp  Leu  Pro  Val  Val  Thr
          355                      360                 365

Glu  Tyr  Glu  Lys  Pro  Ser  Asn  Glu  Thr  Lys  Ile  Glu  Val  Val  His  Cys
     370                      375                 380

Val  Glu  Glu  Val  Gly  Phe  Glu  Val  Met  Gly  Asn  Ser  Thr  Phe
385                      390                 395
```

( 2 ) INFORMATION FOR SEQ ID NO:7:

( i ) SEQUENCE CHARACTERISTICS:
        ( A ) LENGTH: 332 amino acids
        ( B ) TYPE: amino acid
        ( C ) STRANDEDNESS: unknown
        ( D ) TOPOLOGY: linear ( i i ) MOLECULE TYPE: peptide ( x i ) SEQUENCE DESCRIPTION: SEQ ID NO:7:

```
Met  Val  Pro  Val  Leu  Leu  Ile  Leu  Val  Gly  Ala  Leu  Ala  Thr  Leu  Gln
1                   5                   10                          15

Ala  Asp  Leu  Leu  Asn  His  Lys  Lys  Phe  Leu  Leu  Pro  Pro  Val  Asn
               20                  25                       30

Phe  Thr  Ile  Lys  Ala  Thr  Gly  Leu  Ala  Gln  Val  Leu  Leu  His  Trp  Asp
          35                  40                       45

Pro  Asn  Pro  Asp  Gln  Glu  Gln  Arg  His  Val  Asp  Leu  Glu  Tyr  His  Val
     50                  55                       60

Lys  Ile  Asn  Ala  Pro  Gln  Glu  Asp  Glu  Tyr  Asp  Thr  Arg  Lys  Thr  Glu
65                       70                       75                       80
```

-continued

```
Ser  Lys  Cys  Val  Thr  Pro  Leu  His  Glu  Gly  Phe  Ala  Ala  Ser  Val  Arg
               85                       90                       95
Thr  Ile  Leu  Lys  Ser  Ser  His  Thr  Thr  Leu  Ala  Ser  Ser  Trp  Val  Ser
               100                     105                     110
Ala  Glu  Leu  Lys  Ala  Pro  Pro  Gly  Ser  Pro  Gly  Thr  Ser  Val  Thr  Asn
               115                     120                     125
Leu  Thr  Cys  Thr  Thr  His  Thr  Val  Val  Ser  Ser  His  Thr  His  Leu  Arg
          130                     135                     140
Pro  Tyr  Gln  Val  Ser  Leu  Arg  Cys  Thr  Trp  Leu  Val  Gly  Lys  Asp  Ala
145                     150                     155                     160
Pro  Glu  Asp  Thr  Gln  Tyr  Phe  Leu  Tyr  Tyr  Arg  Phe  Gly  Val  Leu  Thr
                    165                     170                     175
Glu  Lys  Cys  Gln  Glu  Tyr  Ser  Arg  Asp  Ala  Leu  Asn  Arg  Asn  Thr  Ala
               180                     185                     190
Cys  Trp  Phe  Pro  Arg  Thr  Phe  Ile  Asn  Ser  Lys  Gly  Phe  Glu  Gln  Leu
               195                     200                     205
Ala  Val  His  Ile  Asn  Gly  Ser  Lys  Arg  Ala  Ala  Ile  Lys  Pro  Phe
          210                     215                     220
Asp  Gln  Leu  Phe  Ser  Pro  Leu  Ala  Ile  Asp  Gln  Val  Asn  Pro  Pro  Arg
225                     230                     235                     240
Asn  Val  Thr  Val  Glu  Ile  Glu  Ser  Asn  Ser  Leu  Tyr  Ile  Gln  Trp  Glu
                    245                     250                     255
Lys  Pro  Leu  Ser  Ala  Phe  Pro  Asp  His  Cys  Phe  Asn  Tyr  Glu  Leu  Lys
               260                     265                     270
Ile  Tyr  Asn  Thr  Lys  Asn  Gly  His  Ile  Gln  Lys  Glu  Lys  Leu  Ile  Ala
          275                     280                     285
Asn  Lys  Phe  Ile  Ser  Lys  Ile  Asp  Asp  Val  Ser  Thr  Tyr  Ser  Ile  Gln
     290                     295                     300
Val  Arg  Ala  Ala  Val  Ser  Ser  Pro  Cys  Arg  Met  Pro  Gly  Arg  Trp  Gly
305                     310                     315                     320
Glu  Trp  Ser  Gln  Pro  Ile  Tyr  Val  Glu  Thr  Phe  Glu
                    325                     330
```

( 2 ) INFORMATION FOR SEQ ID NO:8:

( i ) SEQUENCE CHARACTERISTICS:
        ( A ) LENGTH: 315 amino acids
        ( B ) TYPE: amino acid
        ( C ) STRANDEDNESS: unknown
        ( D ) TOPOLOGY: linear ( i i ) MOLECULE TYPE: peptide ( x i ) SEQUENCE DESCRIPTION: SEQ ID NO:8:

```
Asp  Leu  Leu  Asn  His  Lys  Lys  Phe  Leu  Leu  Leu  Pro  Pro  Val  Asn  Phe
1                   5                       10                      15
Thr  Ile  Lys  Ala  Thr  Gly  Leu  Ala  Gln  Val  Leu  Leu  His  Trp  Asp  Pro
               20                      25                      30
Asn  Pro  Asp  Gln  Glu  Gln  Arg  His  Val  Asp  Leu  Glu  Tyr  His  Val  Lys
          35                      40                      45
Ile  Asn  Ala  Pro  Gln  Glu  Asp  Glu  Tyr  Asp  Thr  Arg  Lys  Thr  Glu  Ser
     50                      55                      60
Lys  Cys  Val  Thr  Pro  Leu  His  Glu  Gly  Phe  Ala  Ala  Ser  Val  Arg  Thr
65                      70                      75                      80
Ile  Leu  Lys  Ser  Ser  His  Thr  Thr  Leu  Ala  Ser  Ser  Trp  Val  Ser  Ala
                    85                      90                      95
Glu  Leu  Lys  Ala  Pro  Pro  Gly  Ser  Pro  Gly  Thr  Ser  Val  Thr  Asn  Leu
```

|     |     |     |     |     | 100 |     |     |     |     | 105 |     |     |     |     | 110 |     |     |
|-----|-----|-----|-----|-----|-----|-----|-----|-----|-----|-----|-----|-----|-----|-----|-----|-----|-----|

Thr Cys Thr Thr His Thr Val Val Ser Ser His Thr His Leu Arg Pro
    115                    120               125

Tyr Gln Val Ser Leu Arg Cys Thr Trp Leu Val Gly Lys Asp Ala Pro
    130                  135               140

Glu Asp Thr Gln Tyr Phe Leu Tyr Tyr Arg Phe Gly Val Leu Thr Glu
145                150              155           160

Lys Cys Gln Glu Tyr Ser Arg Asp Ala Leu Asn Arg Asn Thr Ala Cys
            165            170             175

Trp Phe Pro Arg Thr Phe Ile Asn Ser Lys Gly Phe Glu Gln Leu Ala
        180              185           190

Val His Ile Asn Gly Ser Ser Lys Arg Ala Ala Ile Lys Pro Phe Asp
        195              200           205

Gln Leu Phe Ser Pro Leu Ala Ile Asp Gln Val Asn Pro Pro Arg Asn
    210                215           220

Val Thr Val Glu Ile Glu Ser Asn Ser Leu Tyr Ile Gln Trp Glu Lys
225              230              235          240

Pro Leu Ser Ala Phe Pro Asp His Cys Phe Asn Tyr Glu Leu Lys Ile
            245            250           255

Tyr Asn Thr Lys Asn Gly His Ile Gln Lys Glu Lys Leu Ile Ala Asn
        260              265           270

Lys Phe Ile Ser Lys Ile Asp Asp Val Ser Thr Tyr Ser Ile Gln Val
    275                280           285

Arg Ala Ala Val Ser Ser Pro Cys Arg Met Pro Gly Arg Trp Gly Glu
    290                295           300

Trp Ser Gln Pro Ile Tyr Val Glu Thr Phe Glu
305              310              315

( 2 ) INFORMATION FOR SEQ ID NO:9:

( i ) SEQUENCE CHARACTERISTICS:
        ( A ) LENGTH: 1260 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

```
ATGATCATCG TGGCGCATGT ATTACTCATC CTTTTGGGGG CCACTGAGAT ACTGCAAGCT      60
GACTTACTTC CTGATGAAAA GATTTCACTT CTCCCACCTG TCAATTTCAC CATTAAAGTT     120
ACTGGTTTGG CTCAAGTTCT TTTACAATGG AAACCAAATC CTGATCAAGA GCAAAGGAAT     180
GTTAATCTAG AATATCAAGT GAAAATAAAC GCTCCAAAAG AAGATGACTA TGAAACCAGA     240
ATCACTGAAA GCAAATGTGT AACCATCCTC ACAAAGGCT TTCAGCAAG TGTGCGGACC      300
ATCCTGCAGA ACGACCACTC ACTACTGGCC AGCAGCTGGG CTTCTGCTGA ACTTCATGCC     360
CCACCAGGGT CTCCTGGAAC CTCAGTTGTG AATTTAACTT GCACCACAAA CACTACAGAA     420
GACAATTATT CACGTTTAAG GTCATACCAA GTTTCCCTTC ACTGCACCTG GCTTGTTGGC     480
ACAGATGCCC CTGAGGACAC GCAGTATTTT CTCTACTATA GGTATGGCTC TTGGACTGAA     540
GAATGCCAAG AATACAGCAA AGACACACTG GGGAGAAATA TCGCATGCTG GTTCCCAGG     600
ACTTTTATCC TCAGCAAAGG GCGTGACTGG CTTGCGGTGC TTGTTAACGG CTCCAGCAAG     660
CACTCTGCTA TCAGGCCCTT TGATCAGCTG TTTGCCCTTC ACGCCATTGA TCAAATAAAT     720
CCTCCACTGA ATGTCACAGC AGAGATTGAA GGAACTCGTC TCTCTATCCA ATGGGAGAAA     780
```

-continued

| | | | | | |
|---|---|---|---|---|---|
| CCAGTGTCTG | CTTTTCCAAT | CCATTGCTTT | GATTATGAAG | TAAAAATACA | CAATACAAGG | 840 |
| AATGGATATT | TGCAGATAGA | AAAATTGATG | ACCAATGCAT | TCATCTCAAT | AATTGATGAT | 900 |
| CTTTCTAAGT | ACGATGTTCA | AGTGAGAGCA | GCAGTGAGCT | CCATGTGCAG | AGAGGCAGGG | 960 |
| CTCTGGAGTG | AGTGGAGCCA | ACCTATTTAT | GTGGGAAATG | ATGAACACAA | GCCCTTGAGA | 1020 |
| GAGTGGTTTG | TCATTGTGAT | TATGGCAACC | ATCTGCTTCA | TCTTGTTAAT | TCTCTCGCTT | 1080 |
| ATCTGTAAAA | TATGTCATTT | ATGGATCAAG | TTGTTTCCAC | CAATTCCAGC | ACCAAAAAGT | 1140 |
| AATATCAAAG | ATCTCTTTGT | AACCACTAAC | TATGAGAAAG | CTGGGTCCAG | TGAGACGGAA | 1200 |
| ATTGAAGTCA | TCTGTTATAT | AGAGAAGCCT | GGAGTTGAGA | CCCTGGAGGA | TTCTGTGTTT | 1260 |

( 2 ) INFORMATION FOR SEQ ID NO:10:

( i ) SEQUENCE CHARACTERISTICS:
        ( A ) LENGTH: 2006 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

| | | | | | |
|---|---|---|---|---|---|
| CGGTCCTCGC | CATCTTCTGT | TGAGTACTGG | TCGGAACAAG | AGGATCGTCT | GTAGACAGGA | 60 |
| TATGATCATC | GTGGCGCATG | TATTACTCAT | CCTTTTGGGG | GCCACTGAGA | TACTGCAAGC | 120 |
| TGACTTACTT | CCTGATGAAA | AGATTTCACT | TCTCCCACCT | GTCAATTTCA | CCATTAAAGT | 180 |
| TACTGGTTTG | GCTCAAGTTC | TTTTACAATG | GAAACCAAAT | CCTGATCAAG | AGCAAAGGAA | 240 |
| TGTTAATCTA | GAATATCAAG | TGAAAATAAA | CGCTCCAAAA | GAAGATGACT | ATGAAACCAG | 300 |
| AATCACTGAA | AGCAAATGTG | TAACCATCCT | CCACAAAGGC | TTTTCAGCAA | GTGTGCGGAC | 360 |
| CATCCTGCAG | AACGACCACT | CACTACTGGC | CAGCAGCTGG | GCTTCTGCTG | AACTTCATGC | 420 |
| CCCACCAGGG | TCTCCTGGAA | CCTCAGTTGT | GAATTTAACT | TGCACCACAA | ACACTACAGA | 480 |
| AGACAATTAT | TCACGTTTAA | GGTCATACCA | AGTTTCCCTT | CACTGCACCT | GGCTTGTTGG | 540 |
| CACAGATGCC | CCTGAGGACA | CGCAGTATTT | TCTCTACTAT | AGGTATGGCT | CTTGGACTGA | 600 |
| AGAATGCCAA | GAATACAGCA | AAGACACACT | GGGGAGAAAT | ATCGCATGCT | GGTTTCCCAG | 660 |
| GACTTTTATC | CTCAGCAAAG | GGCGTGACTG | GCTTGCGGTG | CTTGTTAACG | GCTCCAGCAA | 720 |
| GCACTCTGCT | ATCAGGCCCT | TTGATCAGCT | GTTTGCCCTT | CACGCCATTG | ATCAAATAAA | 780 |
| TCCTCCACTG | AATGTCACAG | CAGAGATTGA | AGGAACTCGT | CTCTCTATCC | AATGGGAGAA | 840 |
| ACCAGTGTCT | GCTTTTCCAA | TCCATTGCTT | TGATTATGAA | GTAAAAATAC | ACAATACAAG | 900 |
| GAATGGATAT | TTGCAGATAG | AAAAATTGAT | GACCAATGCA | TTCATCTCAA | TAATTGATGA | 960 |
| TCTTTCTAAG | TACGATGTTC | AAGTGAGAGC | AGCAGTGAGC | TCCATGTGCA | GAGAGGCAGG | 1020 |
| GCTCTGGAGT | GAGTGGAGCC | AACCTATTTA | TGTGGGAAAT | GATGAACACA | AGCCCTTGAG | 1080 |
| AGAGTGGTTT | GTCATTGTGA | TTATGGCAAC | CATCTGCTTC | ATCTTGTTAA | TTCTCTCGCT | 1140 |
| TATCTGTAAA | ATATGTCATT | TATGGATCAA | GTTGTTTCCA | CCAATTCCAG | CACCAAAAAG | 1200 |
| TAATATCAAA | GATCTCTTTG | TAACCACTAA | CTATGAGAAA | GCTGGGTCCA | GTGAGACGGA | 1260 |
| AATTGAAGTC | ATCTGTTATA | TAGAGAAGCC | TGGAGTTGAG | ACCCTGGAGG | ATTCTGTGTT | 1320 |
| TTGACTGTCA | CTTTGGCATC | CTCTGATGAA | CTCACACATG | CCTCAGTGCC | TCAGTGAAAA | 1380 |
| GAACAGGGAT | GCTGGCTCTT | GGCTAAGAGG | TGTTCAGAAT | TTAGGCAACA | CTCAATTTAC | 1440 |
| CTGCGAAGCA | ATACACCCAG | ACACACCAGT | CTTGTATCTC | TTAAAAGTAT | GGATGCTTCA | 1500 |
| TCCAAATCGC | CTCACCTACA | GCAGGGAAGT | TGACTCATCC | AAGCATTTTG | CCATGTTTTT | 1560 |

```
TCTCCCCATG CCGTACAGGG TAGCACCTCC TCACCTGCCA ATCTTTGCAA TTTGCTTGAC      1620

TCACCTCAGA CTTTTCATTC ACAACAGACA GCTTTTAAGG CTAACGTCCA GCTGTATTTA      1680

CTTCTGGCTG TGCCCGTTTG GCTGTTTAAG CTGCCAATTG TAGCACTCAG CTACCATCTG      1740

AGGAAGAAAG CATTTTGCAT CAGCCTGGAG TGAATCATGA ACTTGGATTC AAGACTGTCT      1800

TTTCTATAGC AAGTGAGAGC CACAAATTCC TCACCCCCCT ACATTCTAGA ATGATCTTTT      1860

TCTAGGTAGA TTGTGTATGT GTGTGTATGA GAGAGAGAGA GAGAGAGAGA GAGAGAGAGA      1920

GAGAAATTAT CTCAAGCTCC AGAGGCCTGA TCCAGGATAC ATCATTTGAA ACCAACTAAT      1980

TTAAAAGCAT AATAGAGCTA ATATAT                                          2006
```

( 2 ) INFORMATION FOR SEQ ID NO:11:

( i ) SEQUENCE CHARACTERISTICS:
        ( A ) LENGTH: 1188 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

```
ATGATCATCG TGGCGCATGT ATTACTCATC CTTTTGGGGG CCACTGAGAT ACTGCAAGCT        60

GACTTACTTC CTGATGAAAA GATTTCACTT CTCCCACCTG TCAATTTCAC CATTAAAGTT       120

ACTGGTTTGG CTCAAGTTCT TTTACAATGG AAACCAAATC CTGATCAAGA GCAAAGGAAT       180

GTTAATCTAG AATATCAAGT GAAATAAAC GCTCCAAAAG AAGATGACTA TGAAACCAGA        240

ATCACTGAAA GCAAATGTGT AACCATCCTC CACAAAGGCT TTCAGCAAG TGTGCGGACC        300

ATCCTGCAGA ACGACCACTC ACTACTGGCC AGCAGCTGGG CTTCTGCTGA ACTTCATGCC       360

CCACCAGGGT CTCCTGGAAC CTCAATTGTG AATTTAACTT GCACCACAAA CACTACAGAA       420

GACAATTATT CACGTTTAAG GTCATACCAA GTTTCCCTTC ACTGCACCTG GCTTGTTGGC       480

ACAGATGCCC CTGAGGACAC GCAGTATTTT CTCTACTATA GGTATGGCTC TTGGACTGAA       540

GAATGCCAAG AATACAGCAA AGACACACTG GGGAGAAATA TCGCATGCTG GTTTCCCAGG       600

ACTTTTATCC TCAGCAAAGG GCGTGACTGG CTTGCGGTGC TTGTTAACGG CTCCAGCAAG       660

CACTCTGCTA TCAGGCCCTT TGATCAGCTG TTTGCCCTTC ACGCCATTGA TCAAATAAAT       720

CCTCCACTGA ATGTCACAGC AGAGATTGAA GGAACTCGTC TCTCTATCCA ATGGGAGAAA       780

CCAGTGTCTG CTTTTCCAAT CCATTGCTTT GATTATGAAG TAAAAATACA CAATACAAGG       840

AATGGATATT TGCAGATAGA AAAATTGATG ACCAATGCAT TCATCTCAAT AATTGATGAT       900

CTTTCTAAGT ACGATGTTCA AGTGAGAGCA GCAGTGAGCT CCATGTGCAG AGAGGCAGGG       960

CTCTGGAGTG AGTGGAGCCA ACCTATTTAT GTGGGAAATG ATGAACACAA GCCCTTGAGA      1020

GAGTGGTTTG TCATTGTGAT TATGGCAACC ATCTGCTTCA TCTTGTTAAT TCTCTCGCTT      1080

ATCTGTAAAA TATGTCATTT ATGGATCAAG TTGTTTCCAC CAATTCCAGC ACCAAAAAGT      1140

AATATCAAAG ATCTCTTTGT AACCACTAAC TATGAGAAAG CTGGAATT                   1188
```

( 2 ) INFORMATION FOR SEQ ID NO:12:

( i ) SEQUENCE CHARACTERISTICS:
        ( A ) LENGTH: 2024 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

| | | | | | | |
|---|---|---|---|---|---|---|
| TAGATGCTGG | GGTTGCAGCC | ACGAGCATAG | ACACGACAGA | CACGGTCCTC | GCCATCTTCT | 60 |
| GTTGAGTACT | GGTCGGAACA | AGAGGATCGT | CTGTAGACAG | GATATGATCA | TCGTGGCGCA | 120 |
| TGTATTACTC | ATCCTTTTGG | GGGCCACTGA | GATACTGCAA | GCTGACTTAC | TTCCTGATGA | 180 |
| AAAGATTTCA | CTTCTCCCAC | CTGTCAATTT | CACCATTAAA | GTTACTGGTT | TGGCTCAAGT | 240 |
| TCTTTTACAA | TGGAAACCAA | ATCCTGATCA | AGAGCAAAGG | AATGTTAATC | TAGAATATCA | 300 |
| AGTGAAAATA | AACGCTCCAA | AAGAAGATGA | CTATGAAACC | AGAATCACTG | AAAGCAAATG | 360 |
| TGTAACCATC | CTCCACAAAG | GCTTTTCAGC | AAGTGTGCGG | ACCATCCTGC | AGAACGACCA | 420 |
| CTCACTACTG | GCCAGCAGCT | GGGCTTCTGC | TGAACTTCAT | GCCCCACCAG | GGTCTCCTGG | 480 |
| AACCTCAATT | GTGAATTTAA | CTTGCACCAC | AAACACTACA | GAAGACAATT | ATTCACGTTT | 540 |
| AAGGTCATAC | CAAGTTTCCC | TTCACTGCAC | CTGGCTTGTT | GGCACAGATG | CCCCTGAGGA | 600 |
| CACGCAGTAT | TTTCTCTACT | ATAGGTATGG | CTCTTGGACT | GAAGAATGCC | AAGAATACAG | 660 |
| CAAAGACACA | CTGGGGAGAA | ATATCGCATG | CTGGTTTCCC | AGGACTTTTA | TCCTCAGCAA | 720 |
| AGGGCGTGAC | TGGCTTGCGG | TGCTTGTTAA | CGGCTCCAGC | AAGCACTCTG | CTATCAGGCC | 780 |
| CTTTGATCAG | CTGTTTGCCC | TTCACGCCAT | TGATCAAATA | AATCCTCCAC | TGAATGTCAC | 840 |
| AGCAGAGATT | GAAGGAACTC | GTCTCTCTAT | CCAATGGGAG | AAACCAGTGT | CTGCTTTTCC | 900 |
| AATCCATTGC | TTTGATTATG | AAGTAAAAAT | ACACAATACA | GGAATGGAT | ATTTGCAGAT | 960 |
| AGAAAAATTG | ATGACCAATG | CATTCATCTC | AATAATTGAT | GATCTTTCTA | AGTACGATGT | 1020 |
| TCAAGTGAGA | GCAGCAGTGA | GCTCCATGTG | CAGAGAGGCA | GGGCTCTGGA | GTGAGTGGAG | 1080 |
| CCAACCTATT | TATGTGGGAA | ATGATGAACA | CAAGCCCTTG | AGAGAGTGGT | TTGTCATTGT | 1140 |
| GATTATGGCA | ACCATCTGCT | TCATCTTGTT | AATTCTCTCG | CTTATCTGTA | AAATATGTCA | 1200 |
| TTTATGGATC | AAGTTGTTTC | CACCAATTCC | AGCACCAAAA | AGTAATATCA | AAGATCTCTT | 1260 |
| TGTAACCACT | AACTATGAGA | AAGCTGGAAT | TTAAATTCAA | GCATGTTTTA | ACTTTTGGTT | 1320 |
| TAAGGTACTT | GGGTGTACCT | GGCAGTGTTG | TAAGCTCTTT | ACATTAATTA | ATTAACTCTC | 1380 |
| TAGGTACTGT | TATCTTCATT | TTATAAACAA | GGCAGCTGAA | GTTGAGAGAA | ATAAGTAACC | 1440 |
| TGTCCTAGGT | CACACAATTA | GGAAATGACA | GATCTGGCAG | TCTATTTCCA | GGCAGTCTAT | 1500 |
| TTCCACGAGG | TCATGAGTGC | GAAAGAGGGA | CTAGGGAAG | AATGATTAAC | TCCAGGGAGC | 1560 |
| TGACTTTTCT | AGTGTGCTTA | CCTGTTTTGC | ATCTCTCAAG | GATGTGCCAT | GAAGCTGTAG | 1620 |
| CCAGGTGGAA | TTGTACCACA | GCCCTGACAT | GAACACCTGA | TGGCAGCTGC | TGGGTTGGAG | 1680 |
| CCTAGACAAA | AACATGAAGA | ACCATGGCTG | CTGCCTGAGC | CCATCGTGCT | GTAATTATAG | 1740 |
| AAAACCTTCT | AAGGGAAGAA | TATGCTGATA | TTTTTCAGAT | AAGTACCCCT | TTTATAAAAA | 1800 |
| TCCTCCAAGT | TAGCCCTCGA | TTTTCCATGT | AAGGAAACAG | AGGCTTTGAG | ATAATGTCTG | 1860 |
| TCTCCTAAGG | GACAAAGCCA | GGACTTGATC | CTGTCTTAAA | AATGCAAAAT | GTAGTACTTC | 1920 |
| TTCCATCAAA | GGTAGACATG | CACTAAGGGA | CAGGTTTTGG | CTTGGTATCA | GAATACATTT | 1980 |
| TTAAAAGCTG | TGTAAGAATT | GAACGGGCTG | TACTAGGGGG | TATA | | 2024 |

( 2 ) INFORMATION FOR SEQ ID NO:13:

( i ) SEQUENCE CHARACTERISTICS:
        ( A ) LENGTH: 420 amino acids
        ( B ) TYPE: amino acid
        ( C ) STRANDEDNESS: unknown
        ( D ) TOPOLOGY: linear ( i i ) MOLECULE TYPE: peptide ( x i ) SEQUENCE DESCRIPTION: SEQ ID NO:13:

```
Met Ile Ile Val Ala His Val Leu Leu Ile Leu Leu Gly Ala Thr Glu
 1               5                  10                  15
Ile Leu Gln Ala Asp Leu Leu Pro Asp Glu Lys Ile Ser Leu Leu Pro
            20                  25                  30
Pro Val Asn Phe Thr Ile Lys Val Thr Gly Leu Ala Gln Val Leu Leu
        35                  40                  45
    Gln Trp Lys Pro Asn Pro Asp Gln Glu Gln Arg Asn Val Asn Leu Glu
    50                  55                      60
Tyr Gln Val Lys Ile Asn Ala Pro Lys Glu Asp Tyr Glu Thr Arg
65                  70              75                  80
Ile Thr Glu Ser Lys Cys Val Thr Ile Leu His Lys Gly Phe Ser Ala
                85                  90                  95
Ser Val Arg Thr Ile Leu Gln Asn Asp His Ser Leu Leu Ala Ser Ser
            100                 105                 110
Trp Ala Ser Ala Glu Leu His Ala Pro Gly Ser Pro Gly Thr Ser
        115                 120             125
Val Val Asn Leu Thr Cys Thr Asn Thr Thr Glu Asp Asn Tyr Ser
130                 135                 140
Arg Leu Arg Ser Tyr Gln Val Ser Leu His Cys Thr Trp Leu Val Gly
145                 150                 155                 160
Thr Asp Ala Pro Glu Asp Thr Gln Tyr Phe Leu Tyr Tyr Arg Tyr Gly
                165                 170                 175
Ser Trp Thr Glu Glu Cys Gln Glu Tyr Ser Lys Asp Thr Leu Gly Arg
            180                 185                 190
Asn Ile Ala Cys Trp Phe Pro Arg Thr Phe Ile Leu Ser Lys Gly Arg
        195                 200                 205
Asp Trp Leu Ala Val Leu Val Asn Gly Ser Ser Lys His Ser Ala Ile
210                 215                 220
Arg Pro Phe Asp Gln Leu Phe Ala Leu His Ala Ile Asp Gln Ile Asn
225                 230                 235                 240
Pro Pro Leu Asn Val Thr Ala Glu Ile Glu Gly Thr Arg Leu Ser Ile
                245                 250                 255
Gln Trp Glu Lys Pro Val Ser Ala Phe Pro Ile His Cys Phe Asp Tyr
            260                 265                 270
Glu Val Lys Ile His Asn Thr Arg Asn Gly Tyr Leu Gln Ile Glu Lys
        275                 280                 285
Leu Met Thr Asn Ala Phe Ile Ser Ile Ile Asp Asp Leu Ser Lys Tyr
    290                 295                 300
Asp Val Gln Val Arg Ala Ala Val Ser Ser Met Cys Arg Glu Ala Gly
305                 310                 315                 320
Leu Trp Ser Glu Trp Ser Gln Pro Ile Tyr Val Gly Asn Asp Glu His
                325                 330                 335
Lys Pro Leu Arg Glu Trp Phe Val Ile Val Met Ala Thr Ile Cys
            340                 345                 350
Phe Ile Leu Leu Ile Leu Ser Leu Ile Cys Lys Ile Cys His Leu Trp
        355                 360                 365
Ile Lys Leu Phe Pro Pro Ile Pro Ala Pro Lys Ser Asn Ile Lys Asp
    370                 375                 380
Leu Phe Val Thr Thr Asn Tyr Glu Lys Ala Gly Ser Ser Glu Thr Glu
385                 390                 395                 400
Ile Glu Val Ile Cys Tyr Ile Glu Lys Pro Gly Val Glu Thr Leu Glu
```

|       |       |       | 405   |       |       |       |       | 410   |       |       |       |       | 415   |       |
|-------|-------|-------|-------|-------|-------|-------|-------|-------|-------|-------|-------|-------|-------|-------|

Asp Ser Val Phe
420

(2) INFORMATION FOR SEQ ID NO:14:

(i) SEQUENCE CHARACTERISTICS:
    (A) LENGTH: 396 amino acids
    (B) TYPE: amino acid
    (C) STRANDEDNESS: unknown
    (D) TOPOLOGY: linear (ii) MOLECULE TYPE: peptide (xi) SEQUENCE DESCRIPTION: SEQ ID NO:14:

Met Ile Ile Val Ala His Val Leu Leu Ile Leu Leu Gly Ala Thr Glu
1               5                   10                  15

Ile Leu Gln Ala Asp Leu Leu Pro Asp Glu Lys Ile Ser Leu Leu Pro
            20                  25                  30

Pro Val Asn Phe Thr Ile Lys Val Thr Gly Leu Ala Gln Val Leu Leu
        35                  40                  45

Gln Trp Lys Pro Asn Pro Asp Gln Glu Gln Arg Asn Val Asn Leu Glu
    50                  55                  60

Tyr Gln Val Lys Ile Asn Ala Pro Lys Glu Asp Asp Tyr Glu Thr Arg
65                  70                  75                  80

Ile Thr Glu Ser Lys Cys Val Thr Ile Leu His Lys Gly Phe Ser Ala
                85                  90                  95

Ser Val Arg Thr Ile Leu Gln Asn Asp His Ser Leu Leu Ala Ser Ser
            100                 105                 110

Trp Ala Ser Ala Glu Leu His Ala Pro Pro Gly Ser Pro Gly Thr Ser
        115                 120                 125

Ile Val Asn Leu Thr Cys Thr Thr Asn Thr Thr Glu Asp Asn Tyr Ser
    130                 135                 140

Arg Leu Arg Ser Tyr Gln Val Ser Leu His Cys Thr Trp Leu Val Gly
145                 150                 155                 160

Thr Asp Ala Pro Glu Asp Thr Gln Tyr Phe Leu Tyr Tyr Arg Tyr Gly
                165                 170                 175

Ser Trp Thr Glu Glu Cys Gln Glu Tyr Ser Lys Asp Thr Leu Gly Arg
            180                 185                 190

Asn Ile Ala Cys Trp Phe Pro Arg Thr Phe Ile Leu Ser Lys Gly Arg
        195                 200                 205

Asp Trp Leu Ala Val Leu Val Asn Gly Ser Ser Lys His Ser Ala Ile
    210                 215                 220

Arg Pro Phe Asp Gln Leu Phe Ala Leu His Ala Ile Asp Gln Ile Asn
225                 230                 235                 240

Pro Pro Leu Asn Val Thr Ala Glu Ile Glu Gly Thr Arg Leu Ser Ile
                245                 250                 255

Gln Trp Glu Lys Pro Val Ser Ala Phe Pro Ile His Cys Phe Asp Tyr
            260                 265                 270

Glu Val Lys Ile His Asn Thr Arg Asn Gly Tyr Leu Gln Ile Glu Lys
        275                 280                 285

Leu Met Thr Asn Ala Phe Ile Ser Ile Ile Asp Asp Leu Ser Lys Tyr
    290                 295                 300

Asp Val Gln Val Arg Ala Ala Val Ser Ser Met Cys Arg Glu Ala Gly
305                 310                 315                 320

Leu Trp Ser Glu Trp Ser Gln Pro Ile Tyr Val Gly Asn Asp Glu His
                325                 330                 335

|  |  |  |  |  |  |  |  |  |  |  |  |  |  |  |  |
|---|---|---|---|---|---|---|---|---|---|---|---|---|---|---|---|
| Lys | Pro | Leu | Arg | Glu | Trp | Phe | Val | Ile | Val | Ile | Met | Ala | Thr | Ile | Cys |
|  |  |  | 340 |  |  |  | 345 |  |  |  | 350 |  |  |  |  |
| Phe | Ile | Leu | Leu | Ile | Leu | Ser | Leu | Ile | Cys | Lys | Ile | Cys | His | Leu | Trp |
|  |  |  | 355 |  |  |  | 360 |  |  |  | 365 |  |  |  |  |
| Ile | Lys | Leu | Phe | Pro | Pro | Ile | Pro | Ala | Pro | Lys | Ser | Asn | Ile | Lys | Asp |
|  |  |  | 370 |  |  |  | 375 |  |  |  | 380 |  |  |  |  |
| Leu | Phe | Val | Thr | Thr | Asn | Tyr | Glu | Lys | Ala | Gly | Ile |  |  |  |  |
|  |  |  | 385 |  |  |  | 390 |  |  |  | 395 |  |  |  |  |

( 2 ) INFORMATION FOR SEQ ID NO:15:

( i ) SEQUENCE CHARACTERISTICS:
        ( A ) LENGTH: 1808 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 303..1547

( x i ) SEQUENCE DESCRIPTION: SEQ ID NO:15:

```
GAAATAATTG GTAAACACAG AAAATGTTTC AATAGAAAAA AGAGGAAACA GAACACTGTG      60

TAGCCCTGTT ATCAGCAGAG ACAGAGCTAA CGCTGGGGAT ACCAAACTAG AAGAAGCTCA     120

CTGGACAGGT CCCGGTATGC AGTTCTATTT TTGTTGATGG CTCTGTATCT AATGTGTTCA     180

TTTGTACCAA GGATCTAACC AGGGTCTTCC AGAGTCTGAG CAAGCTTCTC CCACTGAGCT     240

ACATCACAGC CCCCTGTTTA TTGGAAGAAG AAATACTTAC ACCTTTCCAG TATTCGGCTA     300
```

|  |  |  |  |  |  |  |  |  |  |  |  |  |  |  |
|---|---|---|---|---|---|---|---|---|---|---|---|---|---|---|
| CC | ATG | GTG | CCT | GTG | TTA | CTA | ATT | CTT | GTG | GGA | GCT | TTG | GCA | ACA CTG | 347 |
|  | Met | Val | Pro | Val | Leu | Leu | Ile | Leu | Val | Gly | Ala | Leu | Ala | Thr Leu |  |
|  | 1 |  |  |  | 5 |  |  |  |  | 10 |  |  |  | 15 |  |

|  |  |  |  |  |  |  |  |  |  |  |  |  |  |  |
|---|---|---|---|---|---|---|---|---|---|---|---|---|---|---|
| CAA | GCT | GAC | TTA | CTT | AAT | CAC | AAA | AAG | TTT | TTA | CTT | CTA | CCA | CCT GTC | 395 |
| Gln | Ala | Asp | Leu | Leu | Asn | His | Lys | Lys | Phe | Leu | Leu | Leu | Pro | Pro Val |  |
|  |  |  |  | 20 |  |  |  |  | 25 |  |  |  |  | 30 |  |

|  |  |  |  |  |  |  |  |  |  |  |  |  |  |  |
|---|---|---|---|---|---|---|---|---|---|---|---|---|---|---|
| AAT | TTT | ACC | ATT | AAA | GCC | ACT | GGA | TTA | GCT | CAA | GTT | CTT | TTA | CAC TGG | 443 |
| Asn | Phe | Thr | Ile | Lys | Ala | Thr | Gly | Leu | Ala | Gln | Val | Leu | Leu | His Trp |  |
|  |  |  | 35 |  |  |  |  | 40 |  |  |  |  | 45 |  |  |

|  |  |  |  |  |  |  |  |  |  |  |  |  |  |  |
|---|---|---|---|---|---|---|---|---|---|---|---|---|---|---|
| GAC | CCA | AAT | CCT | GAC | CAA | GAG | CAA | AGG | CAT | GTT | GAT | CTA | GAG | TAT CAC | 491 |
| Asp | Pro | Asn | Pro | Asp | Gln | Glu | Gln | Arg | His | Val | Asp | Leu | Glu | Tyr His |  |
|  |  | 50 |  |  |  |  | 55 |  |  |  |  | 60 |  |  |  |

|  |  |  |  |  |  |  |  |  |  |  |  |  |  |  |
|---|---|---|---|---|---|---|---|---|---|---|---|---|---|---|
| GTG | AAA | ATA | AAT | GCC | CCA | CAA | GAA | GAC | GAA | TAT | GAT | ACC | AGA | AAG ACT | 539 |
| Val | Lys | Ile | Asn | Ala | Pro | Gln | Glu | Asp | Glu | Tyr | Asp | Thr | Arg | Lys Thr |  |
|  | 65 |  |  |  |  | 70 |  |  |  |  | 75 |  |  |  |  |

|  |  |  |  |  |  |  |  |  |  |  |  |  |  |  |
|---|---|---|---|---|---|---|---|---|---|---|---|---|---|---|
| GAA | AGC | AAA | TGT | GTG | ACC | CCC | CTT | CAT | GAA | GGC | TTT | GCA | GCT | AGC GTG | 587 |
| Glu | Ser | Lys | Cys | Val | Thr | Pro | Leu | His | Glu | Gly | Phe | Ala | Ala | Ser Val |  |
| 80 |  |  |  |  | 85 |  |  |  |  | 90 |  |  |  | 95 |  |

|  |  |  |  |  |  |  |  |  |  |  |  |  |  |  |
|---|---|---|---|---|---|---|---|---|---|---|---|---|---|---|
| AGG | ACC | ATT | CTG | AAG | AGC | AGC | CAT | ACA | ACT | CTG | GCC | AGC | AGT | TGG GTT | 635 |
| Arg | Thr | Ile | Leu | Lys | Ser | Ser | His | Thr | Thr | Leu | Ala | Ser | Ser | Trp Val |  |
|  |  |  |  | 100 |  |  |  |  | 105 |  |  |  |  | 110 |  |

|  |  |  |  |  |  |  |  |  |  |  |  |  |  |  |
|---|---|---|---|---|---|---|---|---|---|---|---|---|---|---|
| TCT | GCT | GAA | CTC | AAA | GCT | CCA | CCA | GGA | TCT | CCT | GGA | ACC | TCG | GTT ACG | 683 |
| Ser | Ala | Glu | Leu | Lys | Ala | Pro | Pro | Gly | Ser | Pro | Gly | Thr | Ser | Val Thr |  |
|  |  |  |  | 115 |  |  |  |  | 120 |  |  |  |  | 125 |  |

|  |  |  |  |  |  |  |  |  |  |  |  |  |  |  |
|---|---|---|---|---|---|---|---|---|---|---|---|---|---|---|
| AAT | TTA | ACT | TGT | ACC | ACA | CAC | ACT | GTT | GTA | AGT | AGC | CAC | ACC | CAC TTA | 731 |
| Asn | Leu | Thr | Cys | Thr | Thr | His | Thr | Val | Val | Ser | Ser | His | Thr | His Leu |  |
|  |  |  | 130 |  |  |  |  | 135 |  |  |  |  | 140 |  |  |

|  |  |  |  |  |  |  |  |  |  |  |  |  |  |  |
|---|---|---|---|---|---|---|---|---|---|---|---|---|---|---|
| AGG | CCA | TAC | CAA | GTG | TCC | CTT | CGT | TGC | ACC | TGG | CTT | GTT | GGG | AAG GAT | 779 |
| Arg | Pro | Tyr | Gln | Val | Ser | Leu | Arg | Cys | Thr | Trp | Leu | Val | Gly | Lys Asp |  |
|  |  |  | 145 |  |  |  |  | 150 |  |  |  |  | 155 |  |  |

```
GCC CCT GAG GAC ACA CAG TAT TTC CTA TAC TAC AGG TTT GGT GTT TTG      827
Ala Pro Glu Asp Thr Gln Tyr Phe Leu Tyr Tyr Arg Phe Gly Val Leu
160             165                 170                 175

ACT GAA AAA TGC CAA GAA TAC AGC AGA GAT GCA CTG AAC AGA AAT ACT      875
Thr Glu Lys Cys Gln Glu Tyr Ser Arg Asp Ala Leu Asn Arg Asn Thr
            180                 185                 190

GCA TGC TGG TTT CCC AGG ACA TTT ATC AAC AGC AAA GGG TTT GAA CAG      923
Ala Cys Trp Phe Pro Arg Thr Phe Ile Asn Ser Lys Gly Phe Glu Gln
                195                 200                 205

CTT GCT GTG CAC ATT AAT GGC TCA AGC AAG CGT GCT GCA ATC AAG CCC      971
Leu Ala Val His Ile Asn Gly Ser Ser Lys Arg Ala Ala Ile Lys Pro
            210                 215                 220

TTT GAT CAG CTG TTC AGT CCA CTT GCC ATT GAC CAA GTG AAT CCT CCA     1019
Phe Asp Gln Leu Phe Ser Pro Leu Ala Ile Asp Gln Val Asn Pro Pro
225             230                 235

AGG AAT GTC ACA GTG GAA ATT GAA AGC AAT TCT CTC TAT ATA CAG TGG     1067
Arg Asn Val Thr Val Glu Ile Glu Ser Asn Ser Leu Tyr Ile Gln Trp
240             245                 250                 255

GAG AAA CCA CTT TCT GCC TTT CCA GAT CAT TGC TTT AAC TAT GAG CTG     1115
Glu Lys Pro Leu Ser Ala Phe Pro Asp His Cys Phe Asn Tyr Glu Leu
            260                 265                 270

AAA ATT TAC AAC ACA AAA AAT GGT CAC ATT CAG AAG GAA AAA CTG ATC     1163
Lys Ile Tyr Asn Thr Lys Asn Gly His Ile Gln Lys Glu Lys Leu Ile
                275                 280                 285

GCC AAT AAG TTC ATC TCA AAA ATT GAT GAT GTT TCT ACA TAT TCC ATT     1211
Ala Asn Lys Phe Ile Ser Lys Ile Asp Asp Val Ser Thr Tyr Ser Ile
            290                 295                 300

CAA GTG AGA GCA GCT GTG AGC TCA CCT TGC AGA ATG CCA GGA AGG TGG     1259
Gln Val Arg Ala Ala Val Ser Ser Pro Cys Arg Met Pro Gly Arg Trp
305             310                 315

GGC GAG TGG AGT CAA CCT ATT TAT GTG GGA AAG GAA AGG AAG TCC TTG     1307
Gly Glu Trp Ser Gln Pro Ile Tyr Val Gly Lys Glu Arg Lys Ser Leu
320             325                 330                 335

GTA GAA TGG CAT CTC ATT GTG CTC CCA ACA GCT GCC TGC TTC GTC TTG     1355
Val Glu Trp His Leu Ile Val Leu Pro Thr Ala Ala Cys Phe Val Leu
            340                 345                 350

TTA ATC TTC TCA CTC ATC TGC AGA GTG TGT CAT TTA TGG ACC AGG TTG     1403
Leu Ile Phe Ser Leu Ile Cys Arg Val Cys His Leu Trp Thr Arg Leu
                355                 360                 365

TTT CCA CCG GTT CCG GCC CCA AAG AGT AAC ATC AAA GAT CTC CCT GTG     1451
Phe Pro Pro Val Pro Ala Pro Lys Ser Asn Ile Lys Asp Leu Pro Val
        370                 375                 380

GTT ACT GAA TAT GAG AAA CCT TCG AAT GAA ACC AAA ATT GAA GTT GTA     1499
Val Thr Glu Tyr Glu Lys Pro Ser Asn Glu Thr Lys Ile Glu Val Val
385             390                 395

CAT TGT GTG GAA GAG GTT GGA TTT GAA GTC ATG GGA AAT TCC ACG TTT     1547
His Cys Val Glu Glu Val Gly Phe Glu Val Met Gly Asn Ser Thr Phe
400             405                 410                 415

TGATGGCATT TTGCCATTCT GAAATGAACT CATACAGGAC TCCGTGATAA GAGCAAGGAC   1607

TGCTATTTCT TGGCAAGGAG GTATTTCAAA TGAACACTCA GAGCCAGGCG GTGGTAGAGC   1667

TCGCCTTTAA TACCAGCACC TGGGATGCAC AGACGGGAGG ATTTCTGAGT TCGAGGCCAG   1727

CTTGGTCTAT AAAGTGAGTT CCAGGACAGC CAGAGCTACA CAGAGAAACC CTGTCTCGAA   1787

AAAACAAACA AACAAACAAA C                                             1808
```

( 2 ) INFORMATION FOR SEQ ID NO:16:

( i ) SEQUENCE CHARACTERISTICS:
        ( A ) LENGTH: 1355 base pairs
        ( B ) TYPE: nucleic acid -continued ( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 13..1008

( x i ) SEQUENCE DESCRIPTION: SEQ ID NO:16:

```
TATTCGGCTA CC ATG GTG CCT GTG TTA CTA ATT CTT GTG GGA GCT TTG         48
              Met Val Pro Val Leu Leu Ile Leu Val Gly Ala Leu
               1               5                  10

GCA ACA CTG CAA GCT GAC TTA CTT AAT CAC AAA AAG TTT TTA CTT CTA       96
Ala Thr Leu Gln Ala Asp Leu Leu Asn His Lys Lys Phe Leu Leu Leu
         15                  20                  25

CCA CCT GTC AAT TTT ACC ATT AAA GCC ACT GGA TTA GCT CAA GTT CTT      144
Pro Pro Val Asn Phe Thr Ile Lys Ala Thr Gly Leu Ala Gln Val Leu
     30                  35                  40

TTA CAC TGG GAC CCA AAT CCT GAC CAA GAG CAA AGG CAT GTT GAT CTA      192
Leu His Trp Asp Pro Asn Pro Asp Gln Glu Gln Arg His Val Asp Leu
 45                  50                  55                  60

GAG TAT CAC GTG AAA ATA AAT GCC CCA CAA GAA GAC GAA TAT GAT ACC      240
Glu Tyr His Val Lys Ile Asn Ala Pro Gln Glu Asp Glu Tyr Asp Thr
                 65                  70                  75

AGA AAG ACT GAA AGC AAA TGT GTG ACC CCC CTT CAT GAA GGC TTT GCA      288
Arg Lys Thr Glu Ser Lys Cys Val Thr Pro Leu His Glu Gly Phe Ala
             80                  85                  90

GCT AGC GTG AGG ACC ATT CTG AAG AGC AGC CAT ACA ACT CTG GCC AGC      336
Ala Ser Val Arg Thr Ile Leu Lys Ser Ser His Thr Thr Leu Ala Ser
         95                 100                 105

AGT TGG GTT TCT GCT GAA CTC AAA GCT CCA CCA GGA TCT CCT GGA ACC      384
Ser Trp Val Ser Ala Glu Leu Lys Ala Pro Pro Gly Ser Pro Gly Thr
    110                 115                 120

TCG GTT ACG AAT TTA ACT TGT ACC ACA CAC ACT GTT GTA AGT AGC CAC      432
Ser Val Thr Asn Leu Thr Cys Thr Thr His Thr Val Val Ser Ser His
125                 130                 135                 140

ACC CAC TTA AGG CCA TAC CAA GTG TCC CTT CGT TGC ACC TGG CTT GTT      480
Thr His Leu Arg Pro Tyr Gln Val Ser Leu Arg Cys Thr Trp Leu Val
                145                 150                 155

GGG AAG GAT GCC CCT GAG GAC ACA CAG TAT TTC CTA TAC TAC AGG TTT      528
Gly Lys Asp Ala Pro Glu Asp Thr Gln Tyr Phe Leu Tyr Tyr Arg Phe
            160                 165                 170

GGT GTT TTG ACT GAA AAA TGC CAA GAA TAC AGC AGA GAT GCA CTG AAC      576
Gly Val Leu Thr Glu Lys Cys Gln Glu Tyr Ser Arg Asp Ala Leu Asn
        175                 180                 185

AGA AAT ACT GCA TGC TGG TTT CCC AGG ACA TTT ATC AAC AGC AAA GGG      624
Arg Asn Thr Ala Cys Trp Phe Pro Arg Thr Phe Ile Asn Ser Lys Gly
    190                 195                 200

TTT GAA CAG CTT GCT GTG CAC ATT AAT GGC TCA AGC AAG CGT GCT GCA      672
Phe Glu Gln Leu Ala Val His Ile Asn Gly Ser Ser Lys Arg Ala Ala
205                 210                 215                 220

ATC AAG CCC TTT GAT CAG CTG TTC AGT CCA CTT GCC ATT GAC CAA GTG      720
Ile Lys Pro Phe Asp Gln Leu Phe Ser Pro Leu Ala Ile Asp Gln Val
                225                 230                 235

AAT CCT CCA AGG AAT GTC ACA GTG GAA ATT GAA AGC AAT TCT CTC TAT      768
Asn Pro Pro Arg Asn Val Thr Val Glu Ile Glu Ser Asn Ser Leu Tyr
            240                 245                 250

ATA CAG TGG GAG AAA CCA CTT TCT GCC TTT CCA GAT CAT TGC TTT AAC      816
Ile Gln Trp Glu Lys Pro Leu Ser Ala Phe Pro Asp His Cys Phe Asn
        255                 260                 265

TAT GAG CTG AAA ATT TAC AAC ACA AAA AAT GGT CAC ATT CAG AAG GAA      864
```

|  |  |  |  |  |  |  |  |  |  |  |  |  |  |  |  |  |
|---|---|---|---|---|---|---|---|---|---|---|---|---|---|---|---|---|
| Tyr | Glu | Leu | Lys | Ile | Tyr | Asn | Thr | Lys | Asn | Gly | His | Ile | Gln | Lys | Glu |  |
|  | 270 |  |  |  | 275 |  |  |  |  | 280 |  |  |  |  |  |  |
| AAA | CTG | ATC | GCC | AAT | AAG | TTC | ATC | TCA | AAA | ATT | GAT | GAT | GTT | TCT | ACA | 912 |
| Lys | Leu | Ile | Ala | Asn | Lys | Phe | Ile | Ser | Lys | Ile | Asp | Asp | Val | Ser | Thr |  |
| 285 |  |  |  |  | 290 |  |  |  | 295 |  |  |  |  |  | 300 |  |
| TAT | TCC | ATT | CAA | GTG | AGA | GCA | GCT | GTG | AGC | TCA | CCT | TGC | AGA | ATG | CCA | 960 |
| Tyr | Ser | Ile | Gln | Val | Arg | Ala | Ala | Val | Ser | Ser | Pro | Cys | Arg | Met | Pro |  |
|  |  |  |  | 305 |  |  |  | 310 |  |  |  |  | 315 |  |  |  |
| GGA | AGG | TGG | GGC | GAG | TGG | AGT | CAA | CCT | ATT | TAT | GTG | GAA | ACC | TTC | GAA | 1008 |
| Gly | Arg | Trp | Gly | Glu | Trp | Ser | Gln | Pro | Ile | Tyr | Val | Glu | Thr | Phe | Glu |  |
|  |  |  | 320 |  |  |  |  | 325 |  |  |  | 330 |  |  |  |  |

```
TGAAACCAAA ATTGAAGTTG TACATTGTGT GGAAGAGGTT GGATTTGAAG TCATGGGAAA    1068
TTCCACGTTT TGATGGCATT TTGCCATTCT GAAATGAACT CATACAGGAC TCCGTGATAA    1128
GAGCAAGGAC TGCTATTTCT TGGCAAGGAG GTATTTCAAA TGAACACTCA GAGCCAGGCG    1188
GTGGTAGAGC TCGCCTTTAA TACCAGCACC TGGGATGCAC AGACGGGAGG ATTTCTGAGT    1248
TCGAGGCCAG CTTGGTCTAT AAAGTGAGTT CCAGGACAGC CAGAGCTACA CAGAGAAACC    1308
CTGTCTCGAA AAAACAAACA AACAAACAAA CAAACAAAAA TGAACAC                  1355
```

(2) INFORMATION FOR SEQ ID NO:17:

(i) SEQUENCE CHARACTERISTICS:
        (A) LENGTH: 2006 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 62..1324

(xi) SEQUENCE DESCRIPTION: SEQ ID NO:17:

```
CGGTCCTCGC CATCTTCTGT TGAGTACTGG TCGGAACAAG AGGATCGTCT GTAGACAGGA     60
```

|  |  |  |  |  |  |  |  |  |  |  |  |  |  |  |  |  |
|---|---|---|---|---|---|---|---|---|---|---|---|---|---|---|---|---|
| T | ATG | ATC | ATC | GTG | GCG | CAT | GTA | TTA | CTC | ATC | CTT | TTG | GGG | GCC | ACT | 106 |
|  | Met | Ile | Ile | Val | Ala | His | Val | Leu | Leu | Ile | Leu | Leu | Gly | Ala | Thr |  |
|  | 1 |  |  |  | 5 |  |  |  |  | 10 |  |  |  |  | 15 |  |
| GAG | ATA | CTG | CAA | GCT | GAC | TTA | CTT | CCT | GAT | GAA | AAG | ATT | TCA | CTT | CTC | 154 |
| Glu | Ile | Leu | Gln | Ala | Asp | Leu | Leu | Pro | Asp | Glu | Lys | Ile | Ser | Leu | Leu |  |
|  |  |  | 20 |  |  |  |  | 25 |  |  |  |  |  | 30 |  |  |
| CCA | CCT | GTC | AAT | TTC | ACC | ATT | AAA | GTT | ACT | GGT | TTG | GCT | CAA | GTT | CTT | 202 |
| Pro | Pro | Val | Asn | Phe | Thr | Ile | Lys | Val | Thr | Gly | Leu | Ala | Gln | Val | Leu |  |
|  |  |  | 35 |  |  |  |  | 40 |  |  |  |  | 45 |  |  |  |
| TTA | CAA | TGG | AAA | CCA | AAT | CCT | GAT | CAA | GAG | CAA | AGG | AAT | GTT | AAT | CTA | 250 |
| Leu | Gln | Trp | Lys | Pro | Asn | Pro | Asp | Gln | Glu | Gln | Arg | Asn | Val | Asn | Leu |  |
|  |  | 50 |  |  |  |  | 55 |  |  |  |  | 60 |  |  |  |  |
| GAA | TAT | CAA | GTG | AAA | ATA | AAC | GCT | CCA | AAA | GAA | GAT | GAC | TAT | GAA | ACC | 298 |
| Glu | Tyr | Gln | Val | Lys | Ile | Asn | Ala | Pro | Lys | Glu | Asp | Asp | Tyr | Glu | Thr |  |
|  | 65 |  |  |  |  | 70 |  |  |  |  | 75 |  |  |  |  |  |
| AGA | ATC | ACT | GAA | AGC | AAA | TGT | GTA | ACC | ATC | CTC | CAC | AAA | GGC | TTT | TCA | 346 |
| Arg | Ile | Thr | Glu | Ser | Lys | Cys | Val | Thr | Ile | Leu | His | Lys | Gly | Phe | Ser |  |
| 80 |  |  |  |  | 85 |  |  |  |  | 90 |  |  |  |  | 95 |  |
| GCA | AGT | GTG | CGG | ACC | ATC | CTG | CAG | AAC | GAC | CAC | TCA | CTA | CTG | GCC | AGC | 394 |
| Ala | Ser | Val | Arg | Thr | Ile | Leu | Gln | Asn | Asp | His | Ser | Leu | Leu | Ala | Ser |  |
|  |  |  | 100 |  |  |  |  | 105 |  |  |  |  | 110 |  |  |  |
| AGC | TGG | GCT | TCT | GCT | GAA | CTT | CAT | GCC | CCA | CCA | GGG | TCT | CCT | GGA | ACC | 442 |
| Ser | Trp | Ala | Ser | Ala | Glu | Leu | His | Ala | Pro | Pro | Gly | Ser | Pro | Gly | Thr |  |
|  |  | 115 |  |  |  |  | 120 |  |  |  |  | 125 |  |  |  |  |
| TCA | GTT | GTG | AAT | TTA | ACT | TGC | ACC | ACA | AAC | ACT | ACA | GAA | GAC | AAT | TAT | 490 |

-continued

| | | | | | | | | | | | | | | | | |
|---|---|---|---|---|---|---|---|---|---|---|---|---|---|---|---|---|
| | Ser | Val | Val | Asn | Leu | Thr | Cys | Thr | Thr | Asn | Thr | Thr | Glu | Asp | Asn | Tyr |
| | | | 130 | | | | 135 | | | | | 140 | | | | |
| TCA | CGT | TTA | AGG | TCA | TAC | CAA | GTT | TCC | CTT | CAC | TGC | ACC | TGG | CTT | GTT | 538 |
| Ser | Arg | Leu | Arg | Ser | Tyr | Gln | Val | Ser | Leu | His | Cys | Thr | Trp | Leu | Val | |
| | 145 | | | | 150 | | | | | 155 | | | | | | |
| GGC | ACA | GAT | GCC | CCT | GAG | GAC | ACG | CAG | TAT | TTT | CTC | TAC | TAT | AGG | TAT | 586 |
| Gly | Thr | Asp | Ala | Pro | Glu | Asp | Thr | Gln | Tyr | Phe | Leu | Tyr | Tyr | Arg | Tyr | |
| 160 | | | | | 165 | | | | | 170 | | | | | 175 | |
| GGC | TCT | TGG | ACT | GAA | GAA | TGC | CAA | GAA | TAC | AGC | AAA | GAC | ACA | CTG | GGG | 634 |
| Gly | Ser | Trp | Thr | Glu | Glu | Cys | Gln | Glu | Tyr | Ser | Lys | Asp | Thr | Leu | Gly | |
| | | | | 180 | | | | | 185 | | | | | 190 | | |
| AGA | AAT | ATC | GCA | TGC | TGG | TTT | CCC | AGG | ACT | TTT | ATC | CTC | AGC | AAA | GGG | 682 |
| Arg | Asn | Ile | Ala | Cys | Trp | Phe | Pro | Arg | Thr | Phe | Ile | Leu | Ser | Lys | Gly | |
| | | | 195 | | | | | 200 | | | | | 205 | | | |
| CGT | GAC | TGG | CTT | GCG | GTG | CTT | GTT | AAC | GGC | TCC | AGC | AAG | CAC | TCT | GCT | 730 |
| Arg | Asp | Trp | Leu | Ala | Val | Leu | Val | Asn | Gly | Ser | Ser | Lys | His | Ser | Ala | |
| | | 210 | | | | | 215 | | | | | 220 | | | | |
| ATC | AGG | CCC | TTT | GAT | CAG | CTG | TTT | GCC | CTT | CAC | GCC | ATT | GAT | CAA | ATA | 778 |
| Ile | Arg | Pro | Phe | Asp | Gln | Leu | Phe | Ala | Leu | His | Ala | Ile | Asp | Gln | Ile | |
| | 225 | | | | | 230 | | | | | 235 | | | | | |
| AAT | CCT | CCA | CTG | AAT | GTC | ACA | GCA | GAG | ATT | GAA | GGA | ACT | CGT | CTC | TCT | 826 |
| Asn | Pro | Pro | Leu | Asn | Val | Thr | Ala | Glu | Ile | Glu | Gly | Thr | Arg | Leu | Ser | |
| 240 | | | | | 245 | | | | | 250 | | | | | 255 | |
| ATC | CAA | TGG | GAG | AAA | CCA | GTG | TCT | GCT | TTT | CCA | ATC | CAT | TGC | TTT | GAT | 874 |
| Ile | Gln | Trp | Glu | Lys | Pro | Val | Ser | Ala | Phe | Pro | Ile | His | Cys | Phe | Asp | |
| | | | | 260 | | | | | 265 | | | | | 270 | | |
| TAT | GAA | GTA | AAA | ATA | CAC | AAT | ACA | AGG | AAT | GGA | TAT | TTG | CAG | ATA | GAA | 922 |
| Tyr | Glu | Val | Lys | Ile | His | Asn | Thr | Arg | Asn | Gly | Tyr | Leu | Gln | Ile | Glu | |
| | | | 275 | | | | | 280 | | | | | 285 | | | |
| AAA | TTG | ATG | ACC | AAT | GCA | TTC | ATC | TCA | ATA | ATT | GAT | GAT | CTT | TCT | AAG | 970 |
| Lys | Leu | Met | Thr | Asn | Ala | Phe | Ile | Ser | Ile | Ile | Asp | Asp | Leu | Ser | Lys | |
| | | 290 | | | | | 295 | | | | | 300 | | | | |
| TAC | GAT | GTT | CAA | GTG | AGA | GCA | GCA | GTG | AGC | TCC | ATG | TGC | AGA | GAG | GCA | 1018 |
| Tyr | Asp | Val | Gln | Val | Arg | Ala | Ala | Val | Ser | Ser | Met | Cys | Arg | Glu | Ala | |
| | 305 | | | | | 310 | | | | | 315 | | | | | |
| GGG | CTC | TGG | AGT | GAG | TGG | AGC | CAA | CCT | ATT | TAT | GTG | GGA | AAT | GAT | GAA | 1066 |
| Gly | Leu | Trp | Ser | Glu | Trp | Ser | Gln | Pro | Ile | Tyr | Val | Gly | Asn | Asp | Glu | |
| 320 | | | | | 325 | | | | | 330 | | | | | 335 | |
| CAC | AAG | CCC | TTG | AGA | GAG | TGG | TTT | GTC | ATT | GTG | ATT | ATG | GCA | ACC | ATC | 1114 |
| His | Lys | Pro | Leu | Arg | Glu | Trp | Phe | Val | Ile | Val | Ile | Met | Ala | Thr | Ile | |
| | | | | 340 | | | | | 345 | | | | | 350 | | |
| TGC | TTC | ATC | TTG | TTA | ATT | CTC | TCG | CTT | ATC | TGT | AAA | ATA | TGT | CAT | TTA | 1162 |
| Cys | Phe | Ile | Leu | Leu | Ile | Leu | Ser | Leu | Ile | Cys | Lys | Ile | Cys | His | Leu | |
| | | | 355 | | | | | 360 | | | | | 365 | | | |
| TGG | ATC | AAG | TTG | TTT | CCA | CCA | ATT | CCA | GCA | CCA | AAA | AGT | AAT | ATC | AAA | 1210 |
| Trp | Ile | Lys | Leu | Phe | Pro | Pro | Ile | Pro | Ala | Pro | Lys | Ser | Asn | Ile | Lys | |
| | | 370 | | | | | 375 | | | | | 380 | | | | |
| GAT | CTC | TTT | GTA | ACC | ACT | AAC | TAT | GAG | AAA | GCT | GGG | TCC | AGT | GAG | ACG | 1258 |
| Asp | Leu | Phe | Val | Thr | Thr | Asn | Tyr | Glu | Lys | Ala | Gly | Ser | Ser | Glu | Thr | |
| | 385 | | | | | 390 | | | | | 395 | | | | | |
| GAA | ATT | GAA | GTC | ATC | TGT | TAT | ATA | GAG | AAG | CCT | GGA | GTT | GAG | ACC | CTG | 1306 |
| Glu | Ile | Glu | Val | Ile | Cys | Tyr | Ile | Glu | Lys | Pro | Gly | Val | Glu | Thr | Leu | |
| 400 | | | | | 405 | | | | | 410 | | | | | 415 | |
| GAG | GAT | TCT | GTG | TTT | TGACTGTCAC TTTGGCATCC TCTGATGAAC TCACACATGC | | | | | | | | | | | 1361 |
| Glu | Asp | Ser | Val | Phe | | | | | | | | | | | | |
| | | | | 420 | | | | | | | | | | | | |

CTCAGTGCCT CAGTGAAAAG AACAGGGATG CTGGCTCTTG GCTAAGAGGT GTTCAGAATT    1421

TAGGCAACAC TCAATTTACC TGCGAAGCAA TACACCCAGA CACACCAGTC TTGTATCTCT    1481

TAAAAGTATG GATGCTTCAT CCAAATCGCC TCACCTACAG CAGGGAAGTT GACTCATCCA    1541

| | | | | |
|---|---|---|---|---|
| AGCATTTTGC | CATGTTTTTT | CTCCCCATGC | CGTACAGGGT | AGCACCTCCT CACCTGCCAA | 1601 |
| TCTTTGCAAT | TTGCTTGACT | CACCTCAGAC | TTTTCATTCA | CAACAGACAG CTTTTAAGGC | 1661 |
| TAACGTCCAG | CTGTATTTAC | TTCTGGCTGT | GCCCGTTTGG | CTGTTTAAGC TGCCAATTGT | 1721 |
| AGCACTCAGC | TACCATCTGA | GGAAGAAAGC | ATTTTGCATC | AGCCTGGAGT GAATCATGAA | 1781 |
| CTTGGATTCA | AGACTGTCTT | TTCTATAGCA | AGTGAGAGCC | ACAAATTCCT CACCCCCCTA | 1841 |
| CATTCTAGAA | TGATCTTTTT | CTAGGTAGAT | TGTGTATGTG | TGTGTATGAG AGAGAGAGAG | 1901 |
| AGAGAGAGAG | AGAGAGAGAG | AGAAATTATC | TCAAGCTCCA | GAGGCCTGAT CCAGGATACA | 1961 |
| TCATTTGAAA | CCAACTAATT | TAAAAGCATA | ATAGAGCTAA | TATAT | 2006 |

( 2 ) INFORMATION FOR SEQ ID NO:18:

( i ) SEQUENCE CHARACTERISTICS:
        ( A ) LENGTH: 2024 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 104..1291

( x i ) SEQUENCE DESCRIPTION: SEQ ID NO:18:

```
TAGATGCTGG GGTTGCAGCC ACGAGCATAG ACACGACAGA CACGGTCCTC GCCATCTTCT       60

GTTGAGTACT GGTCGGAACA AGAGGATCGT CTGTAGACAG GAT ATG ATC ATC GTG        115
                                               Met Ile Ile Val
                                                 1

GCG CAT GTA TTA CTC ATC CTT TTG GGG GCC ACT GAG ATA CTG CAA GCT        163
Ala His Val Leu Leu Ile Leu Leu Gly Ala Thr Glu Ile Leu Gln Ala
  5              10                  15                  20

GAC TTA CTT CCT GAT GAA AAG ATT TCA CTT CTC CCA CCT GTC AAT TTC        211
Asp Leu Leu Pro Asp Glu Lys Ile Ser Leu Leu Pro Pro Val Asn Phe
              25                  30                  35

ACC ATT AAA GTT ACT GGT TTG GCT CAA GTT CTT TTA CAA TGG AAA CCA        259
Thr Ile Lys Val Thr Gly Leu Ala Gln Val Leu Leu Gln Trp Lys Pro
          40                  45                  50

AAT CCT GAT CAA GAG CAA AGG AAT GTT AAT CTA GAA TAT CAA GTG AAA        307
Asn Pro Asp Gln Glu Gln Arg Asn Val Asn Leu Glu Tyr Gln Val Lys
      55                  60                  65

ATA AAC GCT CCA AAA GAA GAT GAC TAT GAA ACC AGA ATC ACT GAA AGC        355
Ile Asn Ala Pro Lys Glu Asp Asp Tyr Glu Thr Arg Ile Thr Glu Ser
  70                  75                  80

AAA TGT GTA ACC ATC CTC CAC AAA GGC TTT TCA GCA AGT GTG CGG ACC        403
Lys Cys Val Thr Ile Leu His Lys Gly Phe Ser Ala Ser Val Arg Thr
 85                  90                  95                 100

ATC CTG CAG AAC GAC CAC TCA CTA CTG GCC AGC AGC TGG GCT TCT GCT        451
Ile Leu Gln Asn Asp His Ser Leu Leu Ala Ser Ser Trp Ala Ser Ala
                105                 110                 115

GAA CTT CAT GCC CCA CCA GGG TCT CCT GGA ACC TCA ATT GTG AAT TTA        499
Glu Leu His Ala Pro Pro Gly Ser Pro Gly Thr Ser Ile Val Asn Leu
            120                 125                 130

ACT TGC ACC ACA AAC ACT ACA GAA GAC AAT TAT TCA CGT TTA AGG TCA        547
Thr Cys Thr Thr Asn Thr Thr Glu Asp Asn Tyr Ser Arg Leu Arg Ser
        135                 140                 145

TAC CAA GTT TCC CTT CAC TGC ACC TGG CTT GTT GGC ACA GAT GCC CCT        595
Tyr Gln Val Ser Leu His Cys Thr Trp Leu Val Gly Thr Asp Ala Pro
    150                 155                 160
```

```
GAG GAC ACG CAG TAT TTT CTC TAC TAT AGG TAT GGC TCT TGG ACT GAA          643
Glu Asp Thr Gln Tyr Phe Leu Tyr Tyr Arg Tyr Gly Ser Trp Thr Glu
165             170             175             180

GAA TGC CAA GAA TAC AGC AAA GAC ACA CTG GGG AGA AAT ATC GCA TGC          691
Glu Cys Gln Glu Tyr Ser Lys Asp Thr Leu Gly Arg Asn Ile Ala Cys
                185             190             195

TGG TTT CCC AGG ACT TTT ATC CTC AGC AAA GGG CGT GAC TGG CTT GCG          739
Trp Phe Pro Arg Thr Phe Ile Leu Ser Lys Gly Arg Asp Trp Leu Ala
            200             205             210

GTG CTT GTT AAC GGC TCC AGC AAG CAC TCT GCT ATC AGG CCC TTT GAT          787
Val Leu Val Asn Gly Ser Ser Lys His Ser Ala Ile Arg Pro Phe Asp
            215             220             225

CAG CTG TTT GCC CTT CAC GCC ATT GAT CAA ATA AAT CCT CCA CTG AAT          835
Gln Leu Phe Ala Leu His Ala Ile Asp Gln Ile Asn Pro Pro Leu Asn
        230             235             240

GTC ACA GCA GAG ATT GAA GGA ACT CGT CTC TCT ATC CAA TGG GAG AAA          883
Val Thr Ala Glu Ile Glu Gly Thr Arg Leu Ser Ile Gln Trp Glu Lys
245             250             255             260

CCA GTG TCT GCT TTT CCA ATC CAT TGC TTT GAT TAT GAA GTA AAA ATA          931
Pro Val Ser Ala Phe Pro Ile His Cys Phe Asp Tyr Glu Val Lys Ile
                265             270             275

CAC AAT ACA AGG AAT GGA TAT TTG CAG ATA GAA AAA TTG ATG ACC AAT          979
His Asn Thr Arg Asn Gly Tyr Leu Gln Ile Glu Lys Leu Met Thr Asn
            280             285             290

GCA TTC ATC TCA ATA ATT GAT GAT CTT TCT AAG TAC GAT GTT CAA GTG         1027
Ala Phe Ile Ser Ile Ile Asp Asp Leu Ser Lys Tyr Asp Val Gln Val
            295             300             305

AGA GCA GCA GTG AGC TCC ATG TGC AGA GAG GCA GGG CTC TGG AGT GAG         1075
Arg Ala Ala Val Ser Ser Met Cys Arg Glu Ala Gly Leu Trp Ser Glu
        310             315             320

TGG AGC CAA CCT ATT TAT GTG GGA AAT GAT GAA CAC AAG CCC TTG AGA         1123
Trp Ser Gln Pro Ile Tyr Val Gly Asn Asp Glu His Lys Pro Leu Arg
325             330             335             340

GAG TGG TTT GTC ATT GTG ATT ATG GCA ACC ATC TGC TTC ATC TTG TTA         1171
Glu Trp Phe Val Ile Val Ile Met Ala Thr Ile Cys Phe Ile Leu Leu
                345             350             355

ATT CTC TCG CTT ATC TGT AAA ATA TGT CAT TTA TGG ATC AAG TTG TTT         1219
Ile Leu Ser Leu Ile Cys Lys Ile Cys His Leu Trp Ile Lys Leu Phe
            360             365             370

CCA CCA ATT CCA GCA CCA AAA AGT AAT ATC AAA GAT CTC TTT GTA ACC         1267
Pro Pro Ile Pro Ala Pro Lys Ser Asn Ile Lys Asp Leu Phe Val Thr
        375             380             385

ACT AAC TAT GAG AAA GCT GGA ATT TAAATTCAAG CATGTTTTAA CTTTTGGTTT        1321
Thr Asn Tyr Glu Lys Ala Gly Ile
390             395

AAGGTACTTG GGTGTACCTG GCAGTGTTGT AAGCTCTTTA CATTAATTAA TTAACTCTCT       1381
AGGTACTGTT ATCTTCATTT TATAAACAAG GCAGCTGAAG TTGAGAGAAA TAAGTAACCT       1441
GTCCTAGGTC ACACAATTAG GAAATGACAG ATCTGGCAGT CTATTCCAG  GCAGTCTATT       1501
TCCACGAGGT CATGAGTGCG AAAGAGGGAC TAGGGGAAGA ATGATTAACT CCAGGGAGCT       1561
GACTTTTCTA GTGTGCTTAC CTGTTTTGCA TCTCTCAAGG ATGTGCCATG AAGCTGTAGC       1621
CAGGTGGAAT TGTACCACAG CCCTGACATG AACACCTGAT GGCAGCTGCT GGGTTGGAGC       1681
CTAGACAAAA ACATGAAGAA CCATGGCTGC TGCCTGAGCC CATCGTGCTG TAATTATAGA       1741
AAACCTTCTA AGGGAAGAAT ATGCTGATAT TTTTCAGATA AGTACCCCTT TTATAAAAAT       1801
CCTCCAAGTT AGCCCTCGAT TTTCCATGTA AGGAAACAGA GGCTTTGAGA TAATGTCTGT       1861
CTCCTAAGGG ACAAAGCCAG GACTTGATCC TGTCTTAAAA ATGCAAAATG TAGTACTTCT       1921
```

```
TCCATCAAAG  GTAGACATGC  ACTAAGGGAC  AGGTTTTGGC  TTGGTATCAG  AATACATTTT       1981
TAAAAGCTGT  GTAAGAATTG  AACGGGCTGT  ACTAGGGGGT  ATA                          2024
```